(12) United States Patent
Himmelsbach et al.

(10) Patent No.: US 8,853,239 B2
(45) Date of Patent: Oct. 7, 2014

(54) COMPOUNDS, PHARMACEUTICAL COMPOSITIONS AND USES THEREOF

(71) Applicant: Boehringer Ingelheim International GmbH, Ingelheim am Rhein (DE)

(72) Inventors: Frank Himmelsbach, Mittelbiberach (DE); Matthias Eckhardt, Biberach an der Riss (DE); Elke Langkopf, Biberach an der Riss (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 204 days.

(21) Appl. No.: 13/706,602

(22) Filed: Dec. 6, 2012

(65) Prior Publication Data
US 2013/0150401 A1 Jun. 13, 2013

(30) Foreign Application Priority Data

Dec. 9, 2011 (EP) .................. 11192751

(51) Int. Cl.
*C07D 407/04* (2006.01)
*C07D 211/06* (2006.01)
*A61K 31/5365* (2006.01)
*A61K 31/4525* (2006.01)

(52) U.S. Cl.
CPC ............ *C07D 407/04* (2013.01); *C07D 211/06* (2013.01); *A61K 31/5365* (2013.01); *A61K 31/4525* (2013.01)
USPC ............ 514/302; 514/320; 546/115; 546/196

(58) Field of Classification Search
CPC ............... C07D 407/04; C07D 211/06; A61K 31/5365; A61K 31/4525
USPC ............. 546/115, 196; 514/302, 320
See application file for complete search history.

(56) References Cited

U.S. PATENT DOCUMENTS

| 8,729,084 B2 * | 5/2014 | Ye et al. ............ 514/252.18 |
| 2012/0322784 A1 | 12/2012 | Himmelsbach et al. |
| 2013/0018030 A1 | 1/2013 | Himmelsbach et al. |
| 2013/0150401 A1 | 6/2013 | Himmelsbach et al. |

FOREIGN PATENT DOCUMENTS

| WO | 2011140161 A1 | 11/2011 |
| WO | 2012080476 A1 | 6/2012 |
| WO | 2012098217 A1 | 7/2012 |

OTHER PUBLICATIONS

International Search Report for PCT/EP2012/074783 mailed Jan. 3, 2013.

\* cited by examiner

*Primary Examiner* — Niloofar Rahmani
(74) *Attorney, Agent, or Firm* — Michael P. Morris; Timothy X. Witkowski

(57) ABSTRACT

The present invention relates to compounds of formula I,

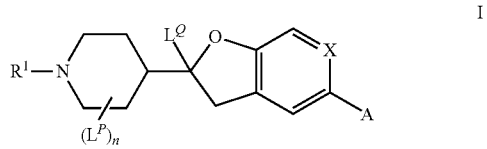

wherein $R^1$, $L^P$, $L^Q$, X, A, and n are as defined in the application, which have valuable pharmacological properties, and in particular bind to the GPR119 receptor and modulate its activity.

9 Claims, No Drawings

COMPOUNDS, PHARMACEUTICAL COMPOSITIONS AND USES THEREOF

FIELD OF THE INVENTION

The present invention relates to new compounds of formula I

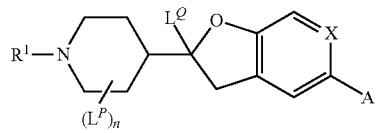

wherein $R^1$, $L^P$, $L^Q$, X, A and n are defined as hereinafter, to processes for preparing these compounds, to their use as modulators of the G-protein-coupled receptor GPR119, to methods for their therapeutic use, in particular in diseases and conditions mediated by the modulation of the G-protein-coupled receptor GPR119, and to pharmaceutical compositions comprising them.

BACKGROUND OF THE INVENTION

Diabetes mellitus is a serious metabolic disease which affects more than 100 million people worldwide. In the USA there are more than 12 million diabetics with 600,000 new cases diagnosed every year. The prevalence of diabetes mellitus is increasing, resulting in a high frequency of complications and a substantial impairment of quality of life and life expectancy. Because of diabetes-associated microvascular complications, in the industrialised countries type 2 diabetes is currently the most common cause of adult-onset loss of vision, renal insufficiency and amputations. In addition, type 2 diabetes is associated with a two- to five-fold increase in the risk of cardiovascular disease.

The UKPDS study (United Kingdom Prospective Diabetes Study) showed that intensive treatment with common therapeutic agents, e.g. metformin, sulphonylureas or insulin, results in only a limited improvement in glycaemic control (difference in the HbA1c value ~0.9%). Moreover, glycaemic control deteriorated considerably over time even in patients in the intensive treatment group, and this was put down to deterioration in beta cell function. Diabetes is also a major cause of damage to the retina at the back of the eye and increases the risk of cataract and glaucoma. Finally, diabetes is associated with nerve damage, particularly in the legs and feet, which affects the patient's ability to feel pain and contributes to serious infections. All in all, complications of diabetes are one of the major causes of death worldwide.

Adiposity (obesity) is the result of an imbalance between calorie intake and energy consumption. It correlates to a high degree with insulin resistance and diabetes. However, the biomolecular mechanisms that are involved in obesity/diabetes syndromes are not yet clear. At an early stage of the development of obesity, an increased insulin secretion balances out the insulin resistance and protects the patient from hyperglycaemia. However, after a time, the beta cell function worsens and non-insulin-dependent diabetes develops in about 20% of the obese population. Obesity has thus become a critical risk factor for diabetes, but the factors that predispose one group of patients to a pathological change in insulin secretion as a response to the accumulation of fat are currently unknown. Obesity also significantly increases the risk of the development of cardiovascular disease. Diabetes is also implicated in the formation of kidney complaints, eye complaints and problems of the nervous system. Kidney disease, also known as nephropathy, sets in when the filtering mechanism of the kidneys is disrupted and proteins escape into the urine in excessive amounts and finally the kidney fails. Therefore there is a medical need for medicaments for preventing and/or treating metabolic disorders (particularly diabetes, predominantly type 2 diabetes) and the complications thereof. In particular there is a need for medicaments with good activity in terms of glycaemic control, disease-modifying properties and reducing cardiovascular morbidity and mortality, and which also have a better safety profile.

Dyslipidemia is a disorder of lipoprotein metabolism, including lipoprotein overproduction or deficiency. Dyslipidemias may be manifested by elevation of the total cholesterol, LDL cholesterol and triglyceride and free fatty acid concentrations, and a decrease in high-density lipoprotein (HDL) cholesterol concentration in the blood. Dyslipidemia occurs often in situations including diabetes, a common cause of lipidemia. For adults with diabetes, it has been recommended that the levels of LDL, HDL, and total cholesterol, and triglyceride be measured every year. Optimal LDL cholesterol levels for adults with diabetes are less than 100 mg/dL (2.60 mmol/L), optimal HDL cholesterol levels are equal to or greater than 40 mg/dL (1.02 mmol/L), and desirable triglyceride levels are less than 150 mg/dL (1.7 mmol/L).

GPR119 is a G-protein coupled receptor (also known as GPCR2, RUP3, SNORF25 or GDIR) which is expressed predominantly in the beta cells of the pancreas and in the K- and L-cells of the intestine. The GPR119 receptor and isoforms have been identified in mammalian species including human, rat, mouse, hamster, chimpanzee, rhesus monkey, cattle and dog. The expression of GPR119 in the pancreas and particularly in the pancreatic β-cells led to the hypothesis that the GPR119 receptor could have effects upon insulin secretion. Activation of the receptor stimulates the cAMP signal pathway, increasing the intracellular levels of cAMP in these cells. This will lead to an improved diabetic situation by a dual action of such a compound: stimulation of cAMP in the beta cell occurs directly via activation of GPR119 in these cells and furthermore indirectly via stimulation of the release of neuroendocrine peptides like GIP and GLP-1 and PYY from the gut. The release of these peptides may have also additional beneficial effects, e.g. on food intake, gastric emptying and other yet unknown functions. Also, a GPR119 agonist can be expected to bring about an improvement in the beta cell function and the beta cell mass. In fact, activation of GPR119 stimulates insulin secretion in-vitro and in-vivo (in rodents) in a glucose-dependent manner. The discovery of two endogenous ligands, lysophosphatidylcholine (LPC) and oleoylethanolamide (OEA) as well as more potent GPR119 agonists have led to the characterization of GPR119 as both an insulin and incretin (GLP-1 and GIP) secretagogue receptor capable of lowering plasma glucose and thereby facilitating glycemic control without the risk of hypoglycemia (Biochem. Biophys. Res. Comm. 2005, 744-751; Cell Metabolism 2006, 167-175; Endocrinology 2007, 2601-9). It has recently been shown that GPR119 agonists effectively lower the blood glucose levels in diabetic rodents without the risk of hypoglycaemia. GPR119 knockout animals have shown that both insulin and incretin secretion induced by GPR119 agonists are dependent upon GPR119 receptor. In addition, it has been shown that GPR119 agonists decrease food intake resulting in weight loss in Sprague Dawley rats. Therefore the GPR119 agonists may be expected to have a therapeutic benefit in metabolic diseases. Examples of such diseases include type 1 diabetes, type 2 diabetes, insufficient glucose tolerance, insulin resistance, hyperglycaemia, hyperlipidaemia, hypercholesterolaemia, dyslipidaemia, syndrome X, metabolic syndrome, obesity, high blood pressure, chronic systemic inflammation, retinopathy, neuropathy, nephropathy, atherosclerosis, endothelial dysfunction and bone-related diseases (such as osteoporosis, rheumatoid arthritis or osteoarthritis). For comparison and additional information also see 1. Dhayal, S., Morgan, N. G. The significance of GPR119 agonists as a future treatment for type 2 diabetes. Drug News Perspect. 2010, 23(7), 418-24.
2. Yoshida, S., Tanaka, H., Oshima, H., Yamazaki, T., Yonetoku, Y., Ohishi, T., Matsui, T., Shibasaki, M. AS1907417, a novel GPR119 agonist, as an insulinotropic and β-cell preservative agent for the treatment of type 2 diabetes. Biochem Biophys Res Commun. 2010, 400(4), 745-51.
3. Jones, R. M., Leonard, J. N., Buzard, D. J., Lehman, J. GPR119 agonists for the treatment of type 2 diabetes. Expert Opinion on Therapeutic Patents 2009, Vol. 19, No. 10: 1339-1359.

SUMMARY OF THE INVENTION

The aim of the present invention is to provide new compounds, in particular new 2,3-dihydro-benzofuran-2-yl-piperidine and 2,3-dihydro-furo[2,3-c]pyridin-2-yl-piperidine derivatives, which are active with regard to the G-protein-coupled receptor GPR119.

Another aim of the present invention is to provide new compounds, in particular new 2,3-dihydro-benzofuran-2-yl-piperidine and 2,3-dihydro-furo[2,3-c]pyridin-2-yl-piperidine derivatives, which are agonists of the G-protein-coupled receptor GPR119.

A further aim of the present invention is to provide new compounds, in particular new 2,3-dihydro-benzofuran-2-yl-piperidine and 2,3-dihydro-furo[2,3-c]pyridin-2-yl-piperidine derivatives, which have an activating effect on the G-protein-coupled receptor GPR119 in vitro and/or in vivo and possess suitable pharmacological and pharmacokinetic properties to use them as medicaments.

A further aim of the present invention is to provide effective GPR119 agonists, in particular for the treatment of metabolic disorders, for example diabetes, dyslipidemia and/or obesity.

A further aim of the present invention is to provide methods for treating a disease or condition mediated by the activation the G-protein-coupled receptor GPR119 in a patient.

A further aim of the present invention is to provide a pharmaceutical composition comprising at least one compound according to the invention.

A further aim of the present invention is to provide a combination of at least one compound according to the invention with one or more additional therapeutic agents.

A further aim of the present invention is to provide methods for the synthesis of the new compounds, in particular 2,3-dihydro-benzofuran-2-yl-piperidine and 2,3-dihydro-furo[2,3-c]pyridin-2-yl-piperidine derivatives.

A further aim of the present invention is to provide starting and/or intermediate compounds suitable in methods for the synthesis of the new compounds.

Further aims of the present invention become apparent to the one skilled in the art by the description hereinbefore and in the following and by the examples.

It has now been found that the compounds according to the invention described in more detail hereinafter have surprising and particularly advantageous properties, and in particular as GPR119 agonists.

In a first aspect the invention thus relates to a compound of formula I

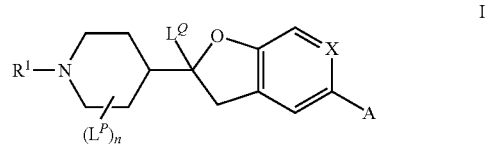

wherein
$R^1$ is selected from the group $R^1$-G1 consisting of $C_{3-6}$-cycloalkyl-$CH_2$— and linear or branched $C_{1-5}$-alkyl-, wherein the $C_{3-6}$-cycloalkyl and the $C_{1-5}$-alkyl group are optionally substituted with one or more F atoms and/or one $CF_3$ group, and wherein the alkyl group may be substituted from position 2 onwards; and A is selected from the group A-G1 consisting of a 1,2,3,6-tetrahydropyridin-4-yl group substituted at the N with $C_{1-4}$-alkyl-$S(=O)_2$—, a piperidin-4-yl group substituted at the N with $C_{1-4}$-alkyl-$S(=O)_2$—, and a phenyl group substituted with a group T and optionally additionally substituted with one or two groups independently selected from F and $CH_3$; and T is selected from the group T-G1 consisting of F, Cl, Br, I, CN, OH, $NO_2$, $C_{1-6}$-alkyl-, $C_{1-6}$-alkenyl-, $C_{1-6}$-alkynyl-, $C_{3-6}$-cycloalkyl, $C_{1-6}$-alkyl-O—, $C_{3-6}$-cycloalkyl-O—, $C_{1-6}$-alkyl-S—, HO—$C(=O)$—, $C_{1-6}$-alkyl-O—C$(=O)$—, $C_{1-4}$-alkyl-C$(=O)$—, $C_{3-6}$-cycloalkyl-C$(=O)$—, $C_{1-4}$-alkyl-$S(=O)$—, $C_{1-4}$-alkyl-$S(=O)_2$—, $R^{NT1}R^{NT2}N$—, $R^{NT1}R^{NT2}N$—C$(=O)$—, $R^{NT1}R^{NT2}N$—S$(=O)_2$—, $R^{NT1}R^{NT2}N$—C$(=O)$—$(R^N)N$—, heterocyclyl, heterocyclyl-O—, aryl, aryl-O—, heteroaryl and heteroaryl-O—, wherein each alkyl, alkenyl, alkynyl, and cycloalkyl group may be optionally substituted with one or more substituents independently of each other selected from F, Cl, CN, OH, $C_{1-3}$-alkyl, $C_{3-6}$-cycloalkyl, $C_{1-3}$-alkyl-O—, $R^{NT1}R^{NT2}N$—, $R^{NT1}R^{NT2}N$—C$(=O)$—, $C_{1-4}$-alkyl-$S(=O)$—, $C_{1-4}$-alkyl-$S(=O)_2$—, $R^{NT1}R^{NT2}N$—S$(=O)_2$— aryl, heteroaryl, and heterocyclyl, and wherein aryl denotes phenyl or naphthyl, and wherein heteroaryl is a 5- or 6-membered aromatic ring which contains 1, 2, 3 or 4 heteroatoms independently of each other selected from N, O and S, wherein the H-atom in one or more NH groups may be optionally replaced by $R^N$; and wherein heterocyclyl is a 4- to 7-membered unsaturated or saturated carbocyclic ring in which 1 or 2 —$CH_2$-groups independently of each other are replaced by $NR^N$, O, —C$(=O)$—, S, —S$(=O)$— or —S$(=O)_2$—, and/or in which a —CH— group is replaced by N; and wherein each aryl, heteroaryl or heterocyclyl group may be optionally substituted with one or more substituents independently of each other selected from $L^A$; and $R^N$ independently of each other is selected from the group $R^N$-G1 consisting of H, $C_{1-4}$-alkyl, $C_{1-4}$-alkyl-C$(=O)$—, and $C_{1-4}$-alkyl-$S(=O)_2$—; and $R^{NT1}$ is selected from the group $R^{NT1}$-G1 consisting of H, $C_{1-6}$-alkyl, $C_{3-6}$-cycloalkyl, $C_{1-6}$-alkyl-C$(=O)$—, $C_{1-6}$-alkyl-$S(=O)_2$, heterocyclyl, aryl and heteroaryl, wherein each alkyl and cylcoalkyl group may be optionally substituted with one or more substituents independently of each other selected from the group consisting of F, OH, CN, $C_{1-4}$-alkyl, $C_{1-4}$-alkyl-O—, $R^N_2N$, $C_{1-4}$-alkyl-$S(=O)_2$—, $C_{3-6}$-cycloalkyl, heterocyclyl, phenyl and heteroaryl; and wherein heterocyclyl may be optionally substituted with one or more substituents independently of each other selected from F, $C_{1-4}$-alkyl, $R^N{}_2N$, OH and $C_{1-4}$-alkyl-O—; and wherein heterocyclyl is a $C_{4-7}$-cycloalkyl ring in which 1 or 2 —$CH_2$-groups independently of each other are replaced by $NR^N$, O, C(=O), S, S(=O) or S(=O)$_2$; and wherein aryl is phenyl or naphthyl; and wherein heteroaryl is a 5- or 6-membered aromatic ring which contains 1, 2 or 3 heteroatoms independently of each other selected from N, O and S, wherein the H-atom in one or more NH groups may be optionally replaced by $R^N$; and wherein aryl and heteroaryl may be optionally substituted with one or more substituents $L^A$; and $R^{NT2}$ is selected from the group $R^{NT2}$-G1 consisting of H and $C_{1-6}$-alkyl; or $R^{NT1}$ and $R^{NT2}$ are linked to form one group selected from the group $R^{NT1}R^{NT2}$-G1 consisting of a $C_{3-5}$-alkylene group, wherein 1 or 2 —$CH_2$-groups independently of each other are replaced by $NR^N$, O, C(=O), S, S(=O) or S(=O)$_2$; and which may be optionally substituted with one or more substituents independently of each other selected from F, $C_{1-4}$-alkyl, $(R^N)_2N$, OH and $C_{1-4}$-alkyl-O—;

$L^A$ is selected from the group $L^A$-G1 consisting of F, Cl, Br, CN, OH, NO$_2$, $C_{1-4}$-alkyl-, $C_{1-4}$-alkyl-O—, $(R^N)_2N$—C(=O), $(R^N)_2N$—, and $C_{1-4}$-alkyl-S(=O)$_2$—, wherein each alkyl group may be optionally substituted with one or more substituents independently of each other selected from F, Cl, CN, OH and $C_{1-3}$-alkyl-O—; and $L^P$ is selected from the group $L^P$-G1 consisting of F and $C_{1-3}$-alkyl, wherein the alkyl group may be substituted with one or more F-atoms; and $L^Q$ is selected from the group $L^Q$-G1 consisting of H and $C_{1-3}$-alkyl; and X is selected from the group X-G1 consisting of CH and N; and n is an integer selected from 0, 1, 2, 3 and 4;

including any tautomers and stereoisomers thereof,
or a salt thereof,
or a solvate or hydrate thereof.

In a further aspect the present invention relates to processes for preparing a compound of general formula I and to new intermediate compounds in these processes.

A further aspect of the invention relates to a salt of the compounds of general formula I according to this invention, in particular to a pharmaceutically acceptable salt thereof.

In a further aspect this invention relates to a pharmaceutical composition, comprising one or more compounds of general formula I or one or more pharmaceutically acceptable salts thereof according to the invention, optionally together with one or more inert carriers and/or diluents.

In a further aspect this invention relates to a method for treating diseases or conditions which are mediated by activating the G-protein-coupled receptor GPR119 in a patient in need thereof characterized in that a compound of general formula I or a pharmaceutically acceptable salt thereof is administered to the patient.

According to another aspect of the invention, there is provided a method for treating a metabolic disease or disorder in a patient in need thereof characterized in that a compound of general formula I or a pharmaceutically acceptable salt thereof is administered to the patient.

According to another aspect of the invention, there is provided the use of a compound of the general formula I or a pharmaceutically acceptable salt thereof for the manufacture of a medicament for a therapeutic method as described hereinbefore and hereinafter.

According to another aspect of the invention, there is provided a compound of the general formula I or a pharmaceutically acceptable salt thereof for use in a therapeutic method as described hereinbefore and hereinafter.

In a further aspect this invention relates to a method for treating a disease or condition mediated by the activation of the G-protein-coupled receptor GPR119 in a patient that includes the step of administering to the patient in need of such treatment a therapeutically effective amount of a compound of the general formula I or a pharmaceutically acceptable salt thereof in combination with a therapeutically effective amount of one or more additional therapeutic agents.

In a further aspect this invention relates to a use of a compound of the general formula I or a pharmaceutically acceptable salt thereof in combination with one or more additional therapeutic agents for the treatment of diseases or conditions which are mediated by the activation of the G-protein-coupled receptor GPR119.

In a further aspect this invention relates to a pharmaceutical composition which comprises a compound according to general formula I or a pharmaceutically acceptable salt thereof and one or more additional therapeutic agents, optionally together with one or more inert carriers and/or diluents.

Other aspects of the invention become apparent to the one skilled in the art from the specification and the experimental part as described hereinbefore and hereinafter.

DETAILED DESCRIPTION

Unless otherwise stated, the groups, residues, and substituents, particularly A, $R^1$, T, $R^N$, $R^{NT1}$, $R^{NT2}$, $L^A$, $L^P$, $L^Q$, X, and n are defined as above and hereinafter. If residues, substituents, or groups occur several times in a compound, as for example $R^N$ or $L^P$, they may have the same or different meanings. Some preferred meanings of individual groups and substituents of the compounds according to the invention will be given hereinafter. Any and each of these definitions may be combined with each other.

$R^1$:

$R^1$-G1:

The group $R^1$ is preferably selected from the group $R^1$-G1 as defined hereinbefore and hereinafter.

$R^1$-G1a:

According to one embodiment the group $R^1$ is selected from the group $R^1$-G1a consisting of $C_{3-6}$-cycloalkyl-$CH_2$— and $C_{1-3}$-alkyl-$CH_2$—, wherein the $C_{3-6}$-cycloalkyl and the $C_{1-3}$-alkyl group are optionally substituted with one to three F atoms and/or one $CF_3$ group.

$R^1$-G2:

According to another embodiment the group $R^1$ is selected from the group $R^1$-G2 consisting of 2-fluoro-2-methyl-propyl and (1-trifluoromethyl-cyclopropyl)-methyl.

$R^1$-G3:

According to one embodiment the group $R^1$ is selected from the group $R^1$-G3 consisting of 2-fluoro-2-methyl-propyl.

$R^1$-G4:

According to one embodiment the group $R^1$ is selected from the group $R^1$-G4 consisting of (1-trifluoromethyl-cyclopropyl)-methyl.

$R^N$ $R^N$-G1:

The group $R^N$ is preferably selected from the group $R^N$-G1 as defined hereinbefore and hereinafter.

$R^N$-G2:

In another embodiment the group $R^N$ is selected from the group $R^N$-G2 consisting of H, $C_{1-3}$-alkyl, $C_{1-3}$-alkyl-carbonyl, and $C_{1-3}$-alkyl-sulfonyl.

$R^N$-G3:

In another embodiment the group $R^N$ is selected from the group $R^N$-G3 consisting of H, methyl, methylcarbonyl, and methylsulfonyl.

A:

A-G1:

The group A is preferably selected from the group A-G1 as defined hereinbefore and hereinafter.

A-G2:

In another embodiment the group A is selected from the group A-G2 consisting of:

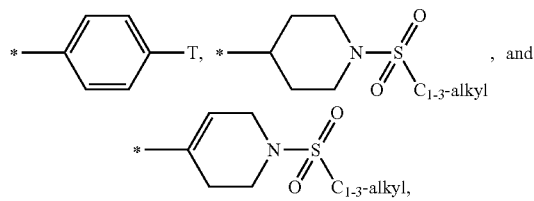

wherein the phenyl group is optionally additionally substituted with one or two groups independently selected from F and $CH_3$, and T is as defined hereinbefore and hereinafter.

A-G3:

In another embodiment the group A is selected from the group A-G3 consisting of:

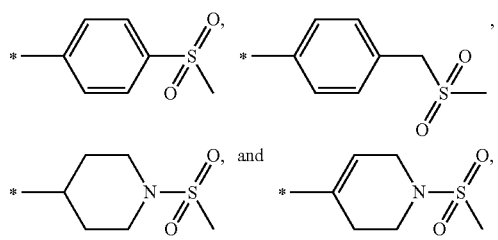

wherein the phenyl groups are optionally substituted with one or two groups independently selected from F and $CH_3$.

A-G3a:

In another embodiment the group A is selected from the group A-G3a consisting of:

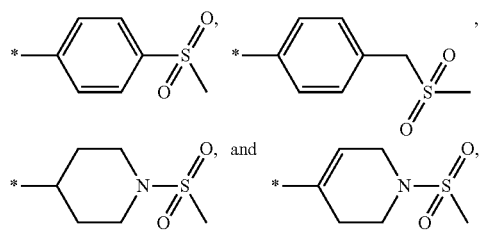

wherein the phenyl groups are optionally substituted with one F-atom.

A-G4:

In another embodiment the group A is selected from the group A-G4 consisting of:

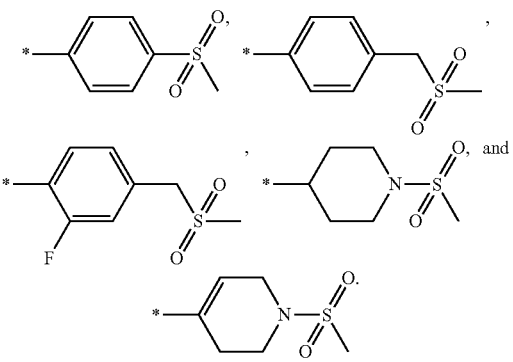

A-G5:

In another embodiment the group A is selected from the group A-G5 consisting of:

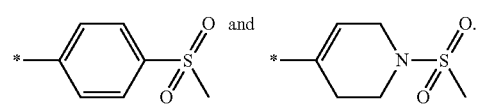 [SMILES: *c1ccc(S(C)(=O)=O)cc1 ; "and" ; *C1=CCN(S(C)(=O)=O)CC1]

T

T-G1:

The group T is preferably selected from the group T-G1 as defined hereinbefore and hereinafter.

T-G2:

According to one embodiment the group T is selected from the group T-G2 consisting of CN, $C_{1-4}$-alkyl-, $C_{1-4}$-alkyl-O—, $C_{1-4}$-alkyl-O—C(=O)—, $C_{1-4}$-alkyl-C(=O)—, $C_{1-4}$-alkyl-S(=O)—, $C_{1-4}$-alkyl-S(=O)$_2$—, $C_{1-4}$-alkyl-S(=O)$_2$—$C_{1-4}$-alkyl-, $R^{NT1}R^{NT2}$N—C(=O)—, $R^{NT1}R^{NT2}$N—S(=O)$_2$—, $C_{1-4}$-alkyl-S(=O)$_2$—$(R^N)$N—, $R^{NT1}R^{NT2}$N, $R^{NT1}R^{NT2}$N—C(=O)—$C_{1-4}$-alkyl-, wherein each alkyl group may be optionally substituted with one or more substituents independently of each other selected from F, Cl, CN, $OCH_3$, and OH.

T-G3:

According to another embodiment the group T is selected from the group T-G3 consisting of CN, $C_{1-4}$-alkyl-S(=O)$_2$—$CH_2$—, $C_{1-4}$-alkyl-S(=O)$_2$—, $R^{NT1}R^{NT2}$N—S(=O)$_2$—, $R^{NT1}R^{NT2}$N—C(=O)—, $C_{1-4}$-alkyl-S(=O)$_2$—$(R^N)$N—, and $R^{NT1}N^{RT2}$N—.

T-G4:

According to another embodiment the group T is selected from the group T-G4 consisting of $C_{1-4}$-alkyl-S(=O)$_2$—$CH_2$— and $C_{1-4}$-alkyl-S(=O)$_2$—.

$R^{NT1}$ $R^{NT1}$-G1:

$R^{NT1}$ is preferably selected from the group $R^{NT1}$-G1 as defined hereinbefore and hereinafter.

$R^{NT1}$-G2:

In another embodiment $R^{NT1}$ is selected from the group $R^{NT1}$-G2 consisting of H, $C_{1-4}$-alkyl and $C_{3-6}$-cycloalkyl, wherein each alkyl and cylcoalkyl group may be optionally substituted with one or two substituents independently of each other selected from the group consisting of F, $CH_3$, OH and $C_{1-3}$-alkyl-O—.

$R^{NT1}$-G3:

In another embodiment $R^{NT1}$ is selected from the group $R^{NT1}$-G3 consisting of H and $C_{1-4}$-alkyl.

$R^{NT2}$ $R^{NT2}$-G1:

$R^{NT2}$ is preferably selected from the group $R^{NT2}$-G1 as defined hereinbefore and hereinafter.

$R^{NT2}$-G2:

In another embodiment $R^{NT2}$ is selected from the group $R^{NT2}$-G2 consisting of H and $C_{1-3}$-alkyl.

$R^{NT2}$-G3:

In another embodiment $R^{NT2}$ is selected from the group $R^{NT2}$-G3 consisting of H and methyl.

$R^{NT2}$-G4:

In another embodiment $R^{NT2}$ is selected from the group $R^{NT2}$-G4 consisting of H.

$R^{NT1}R^{NT2}$ $R^{NT1}R^{NT2}$-G1:

According to one embodiment the groups $R^{NT1}$ and $R^{NT2}$ are linked and form a group which is selected from the group $R^{NT1}R^{NT2}$-G1 as defined hereinbefore and hereinafter.

$R^{NT1}R^{NT2}$-G2:

According to another embodiment the groups $R^{NT1}$ and $R^{NT2}$ are linked and together with the N-atom to which they are attached form a group which is selected from the group $R^{NT1}R^{NT2}$-G2 consisting of azetidinyl, pyrrolidinyl, piperidinyl, morpholinyl, piperazinyl, piperazin-2-onyl, N—$C_{1-3}$-alkyl-piperazinyl, N—$C_{1-3}$-alkyl-piperazin-2-onyl, and N—($C_{1-3}$-alkyl-C(=O))-piperazinyl, which may be optionally substituted with one or more substituents independently of each other selected from the group consisting of F, HO, $C_{1-3}$-alkyl, $C_{1-3}$-alkyl-O—, and $(R^N)_2N$.

$R^{NT1}R^{NT2}$-G3:

According to another embodiment the groups $R^{NT1}$ and $R^{NT2}$ are linked and together with the N-atom to which they are attached form a group which is selected from the group $R^{NT1}R^{NT2}$-G3 consisting of azetidinyl, pyrrolidinyl, piperidinyl and morpholinyl, which may each be optionally substituted with one or two substituents independently of each other selected from the group consisting of F, OH, $CH_3$ and $CH_3$—O—.

$L^A$:

$L^A$-G1:

The group $L^A$ is preferably selected from the group $L^A$-G1 as defined hereinbefore and hereinafter.

$L^A$-G2:

In another embodiment the group $L^A$ is selected from the group $L^A$-G2 consisting of F, Cl, Br, CN, OH, $C_{1-3}$-alkyl-, $C_{1-3}$-alkyl-O—, $H_2N$—, $C_{1-3}$-alkyl-NH— and $(C_{1-3}$-alkyl$)_2N$—, wherein the $C_{1-3}$-alkyl- and $C_{1-3}$-alkyl-O— group may be optionally substituted with one or more F-atoms.

$L^A$-G3:

In another embodiment the group $L^A$ is selected from the group $L^A$-G3 consisting of F, Cl, $CH_3$—, and $CF_3$.

X

X-G1:

The group X is preferably selected from the group X-G1 as defined hereinbefore and hereinafter.

X-G2:

In another embodiment the group X is selected from the group X-G2 consisting of CH.

X-G3:

In another embodiment the group X is selected from the group X-G3 consisting of N.

$L^P$:

$L^P$-G1:

The group $L^P$ is preferably selected from the group $L^P$-G1 as defined hereinbefore and hereinafter.

$L^P$-G2:

In another embodiment the group $L^P$ is selected from the group $L^P$-G2 consisting of F and methyl.

$L^Q$:

$L^Q$-G1:

The group $L^Q$ is preferably selected from the group $L^Q$-G1 as defined hereinbefore and hereinafter.

$L^Q$-G2:

In another embodiment the group $L^Q$ is selected from the group $L^Q$-G2 consisting of H and methyl.

$L^Q$-G3:

In another embodiment the group $L^Q$ is selected from the group $L^Q$-G2 consisting of methyl.

$L^Q$-G4:

In another embodiment the group $L^Q$ is selected from the group $L^Q$-G2 consisting of H.

n:

The index n is an integer selected from 0, 1, 2, 3 or 4.

According to one embodiment the index n is 0, 1 or 2, in particular 0 or 1.

According to another embodiment the index n is 0.

The following preferred embodiments of compounds of the formula I are described using generic formulas (I.1) and (I.2), wherein any tautomers and stereoisomers, solvates, hydrates and salts thereof, in particular the pharmaceutically acceptable salts thereof, are encompassed.

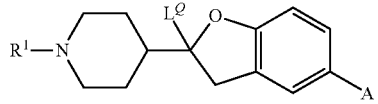

(I.1)

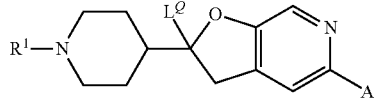

(I.2)

wherein in each of the above formulas (I.1) and (I.2), the groups $R^1$, $L^Q$, and A are defined as hereinbefore and hereinafter.

Further preferred embodiments of compounds of the formula I are described by generic formulas (I.R) and (I.S), wherein any tautomers and stereoisomers, solvates, hydrates and salts thereof, in particular the pharmaceutically acceptable salts thereof, are encompassed.

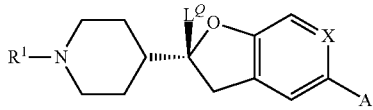

(I.R)

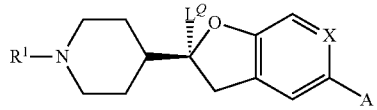

(I.S)

wherein in each of the above formulas (I.R) and (I.S), the groups $R^1$, $L^Q$, X, and A are defined as hereinbefore and hereinafter.

Examples of preferred subgeneric embodiments according to the present invention are set forth in the following table, wherein each substituent group of each embodiment is defined according to the definitions set forth hereinbefore and wherein all other substituents of the formula I are defined according to the definitions set forth hereinbefore:

| Embodiment | Formula | $R^1$- | A- | $L^\varrho$- | X- |
|---|---|---|---|---|---|
| E-1 | I | $R^1$-G1 | A-G1 | $L^\varrho$-G2 | X-G1 |
| E-2 | I | $R^1$-G2 | A-G2 | $L^\varrho$-G2 | X-G1 |
| E-3 | I | $R^1$-G2 | A-G3 | $L^\varrho$-G2 | X-G1 |
| E-4 | I | $R^1$-G2 | A-G4 | $L^\varrho$-G2 | X-G1 |
| E-5 | I | $R^1$-G2 | A-G5 | $L^\varrho$-G2 | X-G1 |
| E-6 | I.1 | $R^1$-G1 | A-G1 | $L^\varrho$-G4 | — |
| E-7 | I.1 | $R^1$-G2 | A-G2 | $L^\varrho$-G4 | — |
| E-8 | I.1 | $R^1$-G2 | A-G3 | $L^\varrho$-G4 | — |
| E-9 | I.1 | $R^1$-G2 | A-G4 | $L^\varrho$-G4 | — |
| E-10 | I.1 | $R^1$-G2 | A-G5 | $L^\varrho$-G4 | — |
| E-11 | I.2 | $R^1$-G1 | A-G1 | $L^\varrho$-G2 | — |
| E-12 | I.2 | $R^1$-G2 | A-G2 | $L^\varrho$-G2 | — |
| E-13 | I.2 | $R^1$-G2 | A-G3 | $L^\varrho$-G2 | — |
| E-14 | I.2 | $R^1$-G2 | A-G4 | $L^\varrho$-G2 | — |
| E-15 | I.2 | $R^1$-G2 | A-G5 | $L^\varrho$-G2 | — |
| E-16 | I.R | $R^1$-G1 | A-G1 | $L^\varrho$-G2 | X-G1 |
| E-17 | I.R | $R^1$-G2 | A-G2 | $L^\varrho$-G2 | X-G1 |
| E-18 | I.R | $R^1$-G2 | A-G3 | $L^\varrho$-G2 | X-G1 |
| E-19 | I.R | $R^1$-G2 | A-G4 | $L^\varrho$-G2 | X-G1 |
| E-20 | I.R | $R^1$-G2 | A-G5 | $L^\varrho$-G2 | X-G1 |
| E-21 | I.S | $R^1$-G1 | A-G1 | $L^\varrho$-G2 | X-G1 |
| E-22 | I.S | $R^1$-G2 | A-G2 | $L^\varrho$-G2 | X-G1 |
| E-23 | I.S | $R^1$-G2 | A-G3 | $L^\varrho$-G2 | X-G1 |
| E-24 | I.S | $R^1$-G2 | A-G4 | $L^\varrho$-G2 | X-G1 |
| E-25 | I.S | $R^1$-G2 | A-G5 | $L^\varrho$-G2 | X-G1 |

Preferred are those compounds of formula I, wherein
X is N;
$R^1$ is

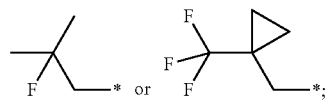

A is

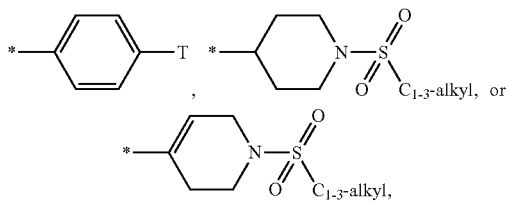

wherein the phenyl group is optionally additionally substituted with one or two groups independently selected from F and $CH_3$;
T is $C_{1-4}$-alkyl-$S(=O)_2$—$CH_2$— or $C_{1-4}$-alkyl-$S(=O)_2$—;
$L^\varrho$ is H or $CH_3$;
n is 0;
and the pharmaceutically acceptable salts thereof.

More preferred are those compounds of formula I, wherein
X is N;
$R^1$ is

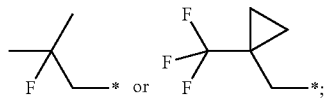

A is

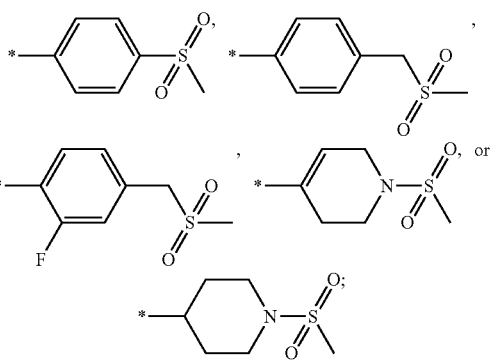

$L^\varrho$ is H or $CH_3$;
n is 0;
and the pharmaceutically acceptable salts thereof.

Particularly preferred compounds, including their tautomers and stereoisomers, the salts thereof, or any solvates or hydrates thereof, are described in the experimental section hereinafter.

The following compounds are mentioned as examples of compounds according to the invention:

(1)
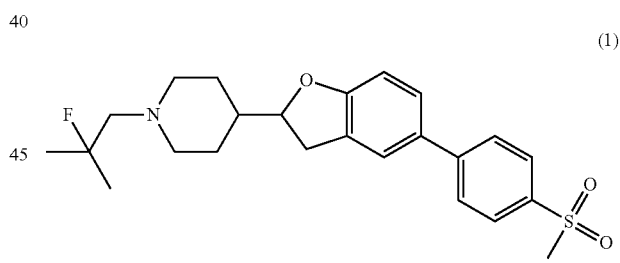

(2)
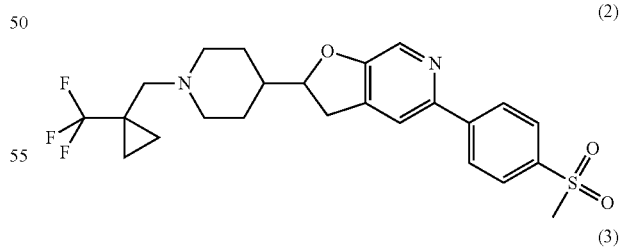

(3)
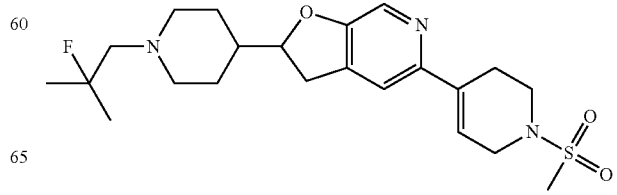

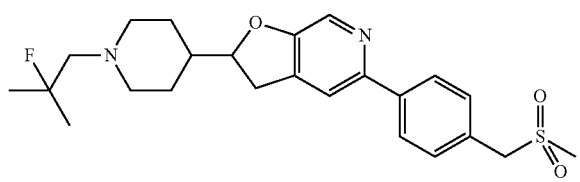
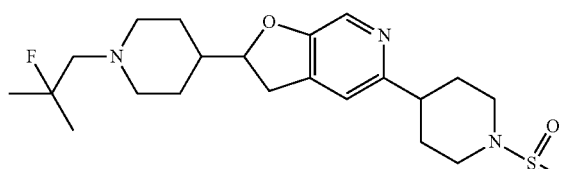
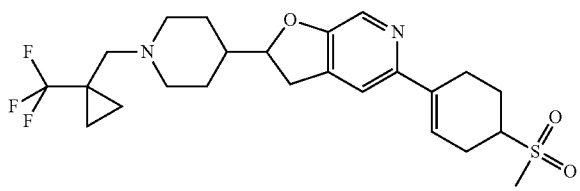
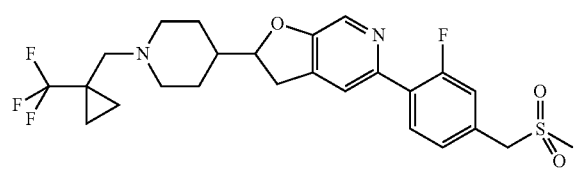

including any tautomers and stereoisomers thereof, or a salt thereof or a solvate or hydrate thereof.

The compounds according to the invention and their intermediates may be obtained using methods of synthesis which are known to the one skilled in the art and described in the literature of organic synthesis. Preferably the compounds are obtained analogously to the methods of preparation explained more fully hereinafter, in particular as described in the experimental section. In some cases the sequence adopted in carrying out the reaction schemes may be varied. Variants of these reactions that are known to the skilled man but are not described in detail here may also be used. The general processes for preparing the compounds according to the invention will become apparent to the skilled man on studying the schemes that follow. Starting compounds are commercially available or may be prepared by methods that are described in the literature or herein, or may be prepared in an analogous or similar manner. Before the reaction is carried out any corresponding functional groups in the compounds may be protected using conventional protecting groups. These protecting groups may be cleaved again at a suitable stage within the reaction sequence using methods familiar to the skilled man.

Compounds of the invention I are accessible using the synthetic route sketched in Scheme 1; $R^1$, $L^P$, n, X, and A have the meanings as defined hereinbefore and hereinafter. Starting with compound 1 the target compounds are obtained upon partial reduction of the benzofuran. The reaction is preferably conducted with hydrogen as the reducing agent in the presence of a transition metal catalyst. Suited transition metals may be derived from Ni, Pd, Pt, Ir, and Rh, such as Raney nickel, Pd on carbon, Pt on carbon, Rh on carbon, $PtO_2$, and $Rh_2O_3$. The reduction is preferably carried out in tetrahydrofuran, acetone, ethyl acetate, alcohol, e.g. methanol, ethanol, or isopropanol, acetic acid, or mixtures thereof, at hydrogen pressures of 1 to 100 bar, at 0 to 120° C. Alternatively, formic acid or a formate salt instead of hydrogen may be used as reducing agent.

The reduction may also be accomplished with a silane or sodium amalgam as reducing agent. Reduction using a silane is for example conducted with triethylsilane and trifluoroacetic acid in dichloromethane, chloroform, acetonitrile, mixtures thereof, or without a solvent in trifluoroacetic acid, at −20 to 120° C. Sodium amalgam is frequently employed in an aqueous solution with sodium hydroxide or sodium bicarbonate.

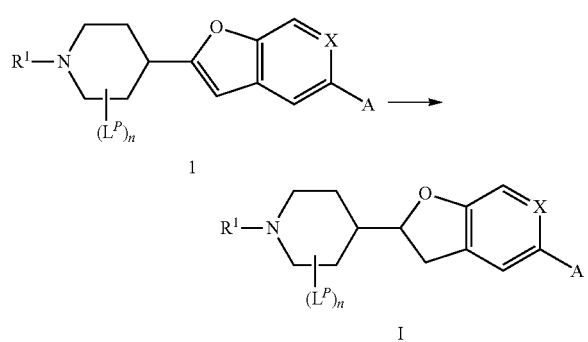

Scheme 1

Compound 1, in turn, may be obtained from compound 4, bearing two replaceable halogen or pseudo-halogen groups, as described in Scheme 2; $R^1$, $L^P$, n, X, and A have the meanings as defined hereinbefore and hereinafter. Depending on the reactivity of the two carbon atoms bearing the halogen or pseudo-halogen groups, the two coupling partners, 6 and 5, are introduced following the sequence depicted on the top or bottom of the scheme. Both residues are preferably attached via a transition metal catalyzed reaction, preferably mediated by a palladium, nickel, copper, or iron species. The active catalyst may be derived from an elemental form of the transition metal, such as palladium on carbon or nanoparticles of iron or palladium, or a salt of the transition metal, such as fluoride, chloride, bromide, acetate, triflate, or trifluoroacetate, which are preferably combined with ligands, such as phosphines, e.g. tri-tert-butylphosphine, tricyclohexylphosphine, optionally substituted biphenyl-dicyclohexyl-phosphines, optionally substituted biphenyl-di-tert-butyl-phosphines, 1,1'-bis(diphenylphosphino)-ferrocene, triphenylphosphine, tritolylphosphine, or trifurylphosphine, phosphites, 1,3-disubstituted imidazole carbenes, 1,3-disubstituted imidazolidine carbenes, dibenzylideneacetone, allyl, or nitriles. A-M is preferably a boronic acid, trifluoroborate, boronic ester, zinc halide, or magnesium halide of A and alkyne 5 is preferably used as is or zinc acetylide. Depending on the nucleophiles the reactions are preferably conducted in benzene, toluene, ether, tetrahydrofuran, 1,2-dimethoxyethane, 1,4-dioxane, N,N-dimethylformamide, N,N-dimethylacetamide, N-methylpyrrolidinone, alcohol, water, or mixtures thereof, at −10 to 160° C. Additives such as halide salts, e.g. lithium chloride, potassium fluoride, tetrabutylammonium fluoride, hydroxide sources, such as potassium hydroxide, potassium carbonate, amines, such as triethylamine, diisopropylamine, and ethyldiisopropylamine, silver salts, such as silver oxide or triflate, and/or copper salts, such as copper iodide or chloride or copper thiophene-2-carboxylate, may be beneficial or even essential for the reaction to proceed. The conditions for the coupling of alkyne 5 with one of the electrophiles, 2 or 4, may bring about the subsequent cyclization as well and thus provide the benzofuran. For instance, with $Pd(PPh_3)_2Cl_2$, CuI, and triethylamine in N,N-dimethylformamide at 20 to 140° C. the benzofuran may be obtained directly. If the intermediate alkyne is obtained the benzofuran may be formed in a separate step using, for example, $Bu_4NF$ in tetrahydrofuran at 50 to 70° C., NaOH in aqueous solution at elevated temperature, CuI or CuCN, optionally in the presence of $NEt_3$, in N,N-dimethylformamide at elevated temperature, $AuCl(PPh_3)$ and $AgOSO_2CF_3$ in $CH_2Cl_2$ or tetrahydrofuran, $AgOSO_2CF_3$, optionally in the presence of trifluoroacetic acid, in $CH_2Cl_2$, Pd, e.g. $PdCl_2$, or other transition metals such as Rh. The benzofuran may also be assembled from a constellation in which the oxygen to cyclize (oxygen at the carbon atom next to the carbon atom bearing the alkynyl group) is embedded in an amide group of an aza-heterocyclic group provided that the additional group on the amide N is cleavable under the reaction conditions (see e.g. *Synthesis* 2007, 3117). The reactivities of the reaction partners (reacting carbons) described may be reversed, i.e. compounds 2, 3, and 4 are the nucleophile bearing M and compounds and 6 are the electrophile bearing $Hal^1$ or $Hal^2$, providing the same products under the same or similar conditions.

Scheme 2

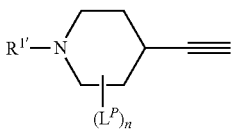

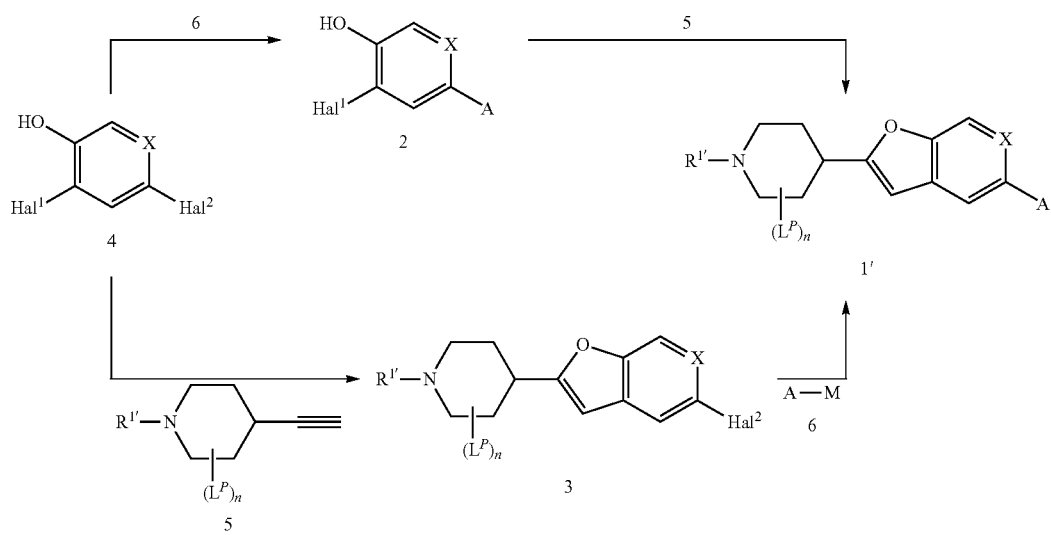

$R^{1'} = R^1$, protective group, e.g., —CO$_2^t$Bu
Hal$^1$, Hal$^2$ = halogen or pseudohalogen, e.g., Cl, Br, I, OSO$_2$CF$_3$, OSO$_2$Me, OSO$_2$aryl
M = metal residue, e.g., B(OH)$_2$, BF$_3$K, B(OCMe$_2$CMe$_2$O), ZnCl/Br/I, MgCl/Br/I Another viable route to synthesize compounds of the invention employs benzofuran derivative 7 as origin (Scheme 3); $R^1$, $L^P$, n, X, and A have the meanings as defined hereinbefore and hereinafter. Compound 7 and piperidine 11 are preferably combined by a transition metal catalyzed process as described above for Scheme 2. The reactivity of the 2-position of the benzofuran 7 determines the suited piperidine 11 for the coupling reaction. Benzofurans bearing Cl, Br, or I at the 2-position are preferably matched with, e.g., tetrahydropyridines bearing for Z B(OH)$_2$, B(OCMe$_2$CMe$_2$O), or BF$_3$K. Reversing the reactivity of 7, i.e. 7 is the nucleophilic partner bearing M, e.g. B(OH)$_2$ or B(OCMe$_2$CMe$_2$O), demands a piperidine of opposite reactivity, i.e. tetrahydropyridines bearing for Z, e.g., OSO$_2$CF$_3$ or Cl. Moreover, piperidin-4-ones (Z═O) may be coupled with electrophilic benzofurans 7 (Y=Cl, Br, I) using tosylhydrazone, a base such as LiOtBu, and a Pd catalyst in a solvent such as 1,4-dioxane (see e.g. *Chem. Eur. J.* 2008, 14, 4792-5, and *Org. Lett.* 2010, 12, 4042-5, and references quoted therein). The additional double-bond in the product due to the use of a tetrahydropyridine may be reduced along with the benzofuran in the next reaction step as described above for Scheme 1. Halogenation with Cl, Br, or I of compound 9 delivers compound 10. Chlorination is accomplished with, for example, N-chlorosuccinimide, chlorine, or sulfuryl chloride. N-chlorosuccinimide is preferably used in the presence of a Lewis acid, e.g. ZrCl$_4$ or HCl, in dichloromethane, acetonitrile, N,N-dimethylformamide, methanol, water, or acetic acid; chlorine is preferably employed in chloroform or acetic acid, and sulfuryl chloride in dichloromethane and chloroform. Bromination is preferably achieved using bromine or N-bromosuccinimide in dichloromethane, acetonitrile, or acetic acid, optionally in the presence of a Lewis acid. Iodine may be introduced with, e.g., iodine combined with silver nitrate, iodine in sulfuric acid, N-iodosuccinimide combined with indium triflate, or iodine chloride in acetic acid or dichloromethane. The concluding step in Scheme 3, transition metal catalyzed coupling of 10 and 6, may be carried out in analogy to the proceeding described above.

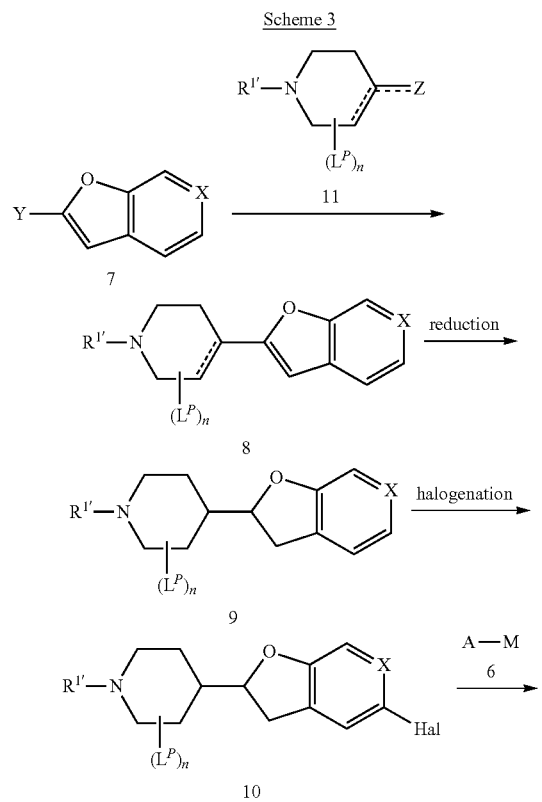

Scheme 3

-continued

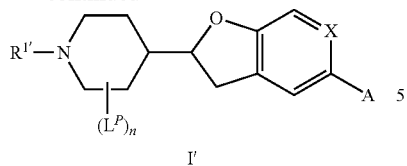

I'

R[1'] = R[1], protective group, e.g., —CO$_2$[t]Bu
Hal = Cl, Br, I
M = metal residue, e.g., B(OH)$_2$, B(OCMe$_2$CMe$_2$O), BF$_3$K, ZnCl/Br/I, MgCl/Br/I
Y = e.g., Hal, OSO$_2$CF$_3$, OSO$_2$Me, OSO$_2$Ph, M, H
Z = e.g., Hal, OSO$_2$CF$_3$, M, ═O
- - - - = single or double bond Scheme 4 shows another way of synthesis of compounds of the invention; R[1], L[P], L[Q], n, X, and A have the meanings as defined hereinbefore and hereinafter. The sequence commences with addition of hydride or an alkyl group to ketone 12 to obtain alcohol 13. Hydride addition is preferably conducted with a complex metal hydride, such as sodium borohydride, lithium borohydride, lithium triethylborohydride, diisobutylaluminum hydride, or lithium aluminum hydride. Sodium borohydride is usually used in aqueous or alcoholic solutions at −20 to 100° C., while the other reagents are preferably employed in dichloromethane, 1,2-dichloroethane, hexanes, ether, 1,4-dioxane, tetrahydrofuran, N-methylpyrrolidone, benzene, toluene, or mixtures thereof, at −80 to 60° C. The reduction may also be conducted in a stereoselective fashion to access only one enantiomer using, e.g., the conditions of the Corey-Bakshi-Shibata (CBS) reduction (also called Corey-Itsuno reduction). Addition of an alkyl group may be accomplished by adding an alkyl lithium or magnesium halide to ketone 12. The reaction is preferably conducted in tetrahydrofuran, ether, toluene, hexanes, or mixtures thereof at −78 to 0° C. The addition of lanthanide salts, e.g. CeCl$_3$, can be beneficial to the reaction. Intramolecular substitution of the leaving group LG with oxygen provides target compound I″. For LG equals F, SO$_2$C$_{1-4}$-alkyl, SO$_2$-aryl, or NO$_2$, the reaction is preferably carried out in the presence of a base, such as NaH, CaH$_2$, BuLi, KO[t]Bu, or KOH, in toluene, tetrahydrofuran, 1,4-dioxane, N,N-dimethylformamide, N,N-dimethylacetamide, N-methylpyrrolidone, or mixtures thereof, at 20 to 200° C. For LG is Cl, Br, or I, the reaction is preferably conducted in the presence of a transition metal catalyst, such as a Pd or Cu species.

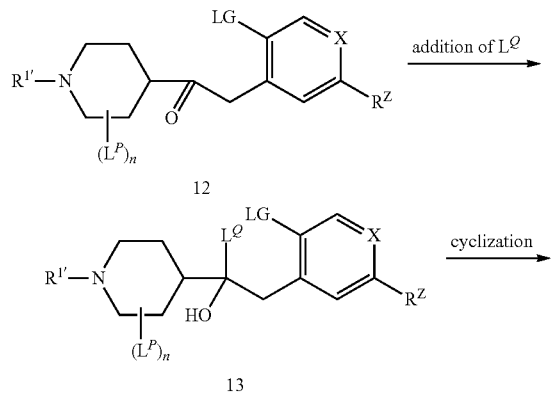

Scheme 4

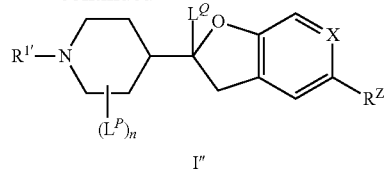

I″

LG = leaving group, e.g., F, Cl, Br, I, OSO$_2$C$_{1-4}$-alkyl, SO$_2$-aryl, NO$_2$
R[Z] = A or group that allows introduction of A, e.g., as described above
R[1'] = R[1], protective group, e.g., —CO$_2$[t]Bu The dihydrofuran ring may also be formed from compound 13', bearing an additional hydroxy group on the aromatic ring. Intramolecular substitution of the aliphatic OH group with the aromatic O group may be accomplished using a phosphine and an azodicarboxylic ester or amide in tetrahydrofuran, 1,4-dioxane, diethyl ether, toluene, benzene, dichloromethane, or mixtures thereof, at −30 to 100° C. (Mitsunobu reaction). Common combinations for this transformation are triphenylphosphine or tributylphosphine and dimethyl azodicarboxylate, diethyl azodicarboxylate, diisopropyl azodicarboxylate, di-(4-chlorobenzyl) azodicarboxylate, dibenzyl azodicarboxylate, di-tert-butyl azodicarboxylate, azodicarboxylic acid bis-(dimethylamide), azodicarboxylic acid dipiperidide, or azodicarboxylic acid dimorpholide. Alternatively, the aliphatic OH group may be transformed into a leaving group, such as Cl, Br, I, OSO$_2$CH$_3$, and OSO$_2$Ph, and then displaced with the aromatic O under basic conditions. Suited bases may be, for instance, carbonates, e.g. Cs$_2$CO$_3$ and K$_2$CO$_3$, hydrides, e.g. NaH, alcoholates, e.g. NaOMe and KO[t]Bu, hydroxides, e.g. KOH and NaOH, that are preferably employed in toluene, tetrahydrofuran, N,N-dimethylformamide, N,N-dimethylacetamide, N-methylpyrrolidinone, dimethyl sulfoxide, alcohol, water, and mixtures thereof. The reaction may be carried out such that the aliphatic hydroxy group is substituted with complete inversion of configuration delivering an enantiomerically enriched or pure product provided that an enantiomerically enriched or pure starting compound is used.

Scheme 5

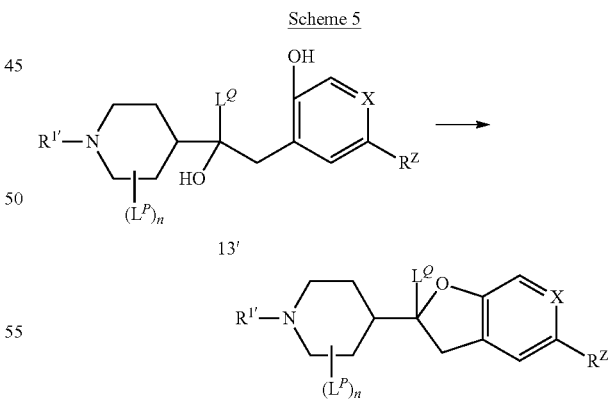

R[1'] = R[1], protective group, e.g., —CO$_2$[t]Bu
R[Z] = A or group that allows introduction of A, e.g., as described above Intermediate 12 may be accessed as delineated in Scheme 6; R[1], L[P], n, X, and A have the meanings as defined hereinbefore and hereinafter. A carboxylic acid derivative 14 can be merged with an aromatic compound 15, that bears an anionic carbon center attached to the aromatic ring, to provide intermediate 12' (route a.). Suited carboxylic acid derivatives may be e.g. carboxylic halides, carboxylic esters, carboxylic anhydrides, and carboxylic amides, while suited nucleophile precursors 15 are preferably derived from an electron deficient aromatic or heteroaromatic, e.g., pyridine, or bear an electron-withdrawing group (EWG) at the carbon center to generate the negative charge more easily; preferred EWG are carboxylic esters and cyano. The reaction is mediated by a base that deprotonates compound 15 to generate the anion which, in turn, adds to the carboxylic function of 14 to give 12'; the anion generating step may be carried out in the presence or prior to the addition of compound 14. Most preferred bases are selected from alcoholates, e.g. KO$^t$Bu and NaOMe, amines, e.g. triethylamine and 1,8-diazabicyclo[5.4.0]undec-7-ene, carbonates, e.g. $Cs_2CO_3$ and $K_2CO_3$, hydroxides, e.g. NaOH and KOH, and amides, e.g. $LiN(SiMe_3)_2$ and $LiN^iPr_2$, that, depending on their reactivity and compatibility, may be used in solvents such as toluene, tetrahydrofuran, 1,4-dioxane, N,N-dimethylformamide, N,N-dimethylacetamide, N-methylpyrrolidinone, dimethyl sulfoxide, alcohol, or mixtures thereof. For example, a compound 14 bearing an ester function (Y=O—$C_{1-4}$-alkyl) may be combined with a compound 15 bearing a cyano or ester group (EWG=CN or C(=O)O$C_{1-4}$-alkyl) using KO$^t$Bu or NaOEt as base and tetrahydrofuran, N-methylpyrrolidinone, or ethanol as solvent. The product 12' may be transformed into intermediate 12 by hydrolysis of the ester or cyano group followed by decarboxylation of the resulting carboxylic acid function. EWG groups such as nitro or sulfonyl can be removed as well.

Combination of compounds 16 and 17 is another way of synthesis for intermediate 12 (route b.). Depending on the reactivity of the coupling partners, the reaction is best conducted in the presence of a transition metal catalyst or without an additive. For example, compound 16 bearing a boronic acid (M=B(OH)$_2$) and compound 17 having a carboxylic chloride (Z=Cl) may be coupled using a Pd catalyst, e.g. Pd(PPh$_3$)$_4$, and a base, e.g. $K_3PO_4$, in a solvent, e.g. toluene or 1,4-dioxane, at 60 to 120° C. A compound 16 with M=Li or MgCl may be matched with an electrophile 17 bearing a carboxamide group (Z=N(OMe)Me). The reaction is commonly conducted in tetrahydrofuran, 1,4-dioxane, ether, toluene, or mixtures thereof, at −70 to 40° C., optionally in the presence of an additive such as $CeCl_3$. Compound 12″ may be converted to intermediate 12 by reduction of the double bond with hydrogen or a formate salt in the presence of a transition metal, e.g. Pd on carbon, or a hydride, e.g. [CuH(PPh$_3$)]$_6$.

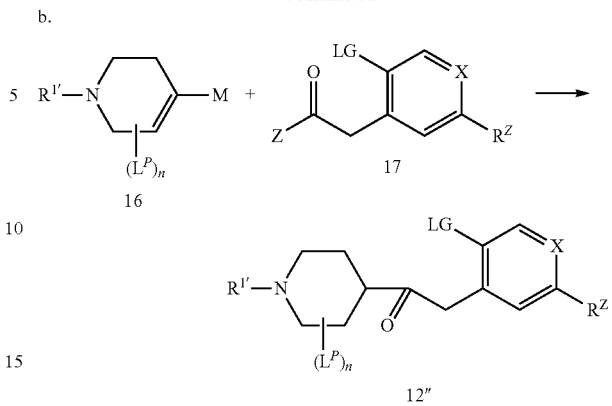

$R^{1'} = R^1$, protective group, e.g., —CO$_2^t$Bu
$R^Z$ = A or group that allows introduction of A, e.g., as described above
EWG = H or electron withdrawing group, e.g., CO$_2$C$_{1-4}$-alkyl, CN, SO$_2$C$_{1-4}$-alkyl, NO$_2$
LG = leaving group, e.g., F, Cl, Br, I, SO$_2$C$_{1-4}$-alkyl, SO$_2$-aryl, NO$_2$
M = metal residue, e.g., B(OH)$_2$, BF$_3$K, B(OCMe$_2$CMe$_2$O), ZnCl/Br/I, MgCl/Br/I, CeCl$_2$
Z = leaving group, e.g., Cl, OC$_{1-4}$-alkyl, N(OMe)Me A general way of attaching residue $R^1$ to the N atom of the piperidine of the compounds of the invention or an intermediate towards them is sketched in Scheme 7; $R^1$, $L^P$, and n have the meanings as defined hereinbefore and hereinafter. The residue $R^1$ may be attached to the piperidine N using an electrophilic $R^1$ group, bearing a leaving group at the CH$_2$ unit to be attached such as Cl, Br, I, OSO$_2$C$_{1-4}$-alkyl, OSO$_2$aryl, or OSO$_2$CF$_3$, in the presence of a base, e.g. Na$_2$CO$_3$, K$_2$CO$_3$, or Cs$_2$CO$_3$, pyridine, 4-dimethylaminopyridine, triethylamine, ethyldiisopropylamine, 1,8-diazabicylo[5.4.0]undec-7-ene, in a solvent such as toluene, tetrahydrofuran, 1,4-dioxane, 1,2-dimethoxyethane, acetonitrile, N,N-dimethylformamide, N,N-dimethylacetamide, N-methylpyrrolidinone, water, methanol, ethanol, isopropanol, dimethyl sulfoxide, or mixtures thereof, at 20 to 220° C. by conventional or microwave heating. Alternatively, the piperidine 18 may be transformed into the corresponding metal piperidide by deprotonation with a strong base, e.g. butyl lithium, NaH, or KH, prior to the addition of the electrophile 19.

Scheme 6

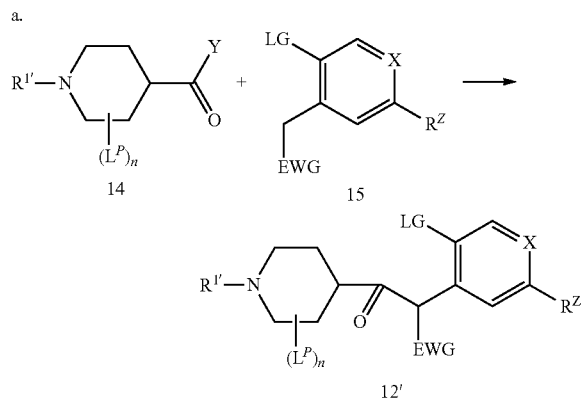

Scheme 7

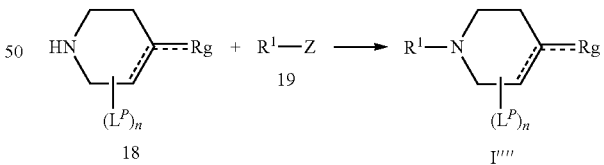

Rg = group that allows attachment of or is missing residue to obtain compounds of general formula I, e.g., see respective compounds outlined above
Z = leaving group, e.g., Cl, Br, I, OSO$_2$CF$_3$, OSO$_2$C$_{1-4}$-alkyl, OSO$_2$-aryl
- - - - - = single or double bond Alternatively, residue $R^1$ may be attached to the N in compound 18 by reductive alkylation employing $R^1$ as aldehyde and a reducing agent, such as NaH$_3$BCN or NaHB(O$_2$CCH$_3$)$_3$, or via a two step sequence by attaching a carboxylic acid derivative of $R^1$ first and reducing subsequently the resulting carboxamide.

The synthetic routes presented may rely on the use of protecting groups. For example, potentially reactive groups present, such as hydroxy, carbonyl, carboxy, amino, alkylamino, or imino, may be protected during the reaction by conventional protecting groups which are cleaved again after the reaction. Suitable protecting groups for the respective functionalities and their removal are well known to the one skilled in the art and are described in the literature of organic synthesis.

The compounds of general formula I may be resolved into their enantiomers and/or diastereomers as mentioned before. Thus, for example, cis/trans mixtures may be resolved into their cis and trans isomers and racemic compounds may be separated into their enantiomers.

The cis/trans mixtures may be resolved, for example, by chromatography into the cis and trans isomers thereof. The compounds of general formula I which occur as racemates may be separated by methods known per se into their optical antipodes and diastereomeric mixtures of compounds of general formula I may be resolved into their diastereomers by taking advantage of their different physico-chemical properties using methods known per se, e.g. chromatography and/or fractional crystallization; if the compounds obtained thereafter are racemates, they may be resolved into the enantiomers as mentioned above.

The racemates are preferably resolved by column chromatography on chiral phases or by crystallization from an optically active solvent or by reacting with an optically active substance which forms salts or derivatives such as esters or amides with the racemic compound. Salts may be formed with enantiomerically pure acids for basic compounds and with enantiomerically pure bases for acidic compounds. Diastereomeric derivatives are formed with enantiomerically pure auxiliary compounds, e.g. acids, their activated derivatives, or alcohols. Separation of the diastereomeric mixture of salts or derivatives thus obtained may be achieved by taking advantage of their different physico-chemical properties, e.g. differences in solubility; the free antipodes may be released from the pure diastereomeric salts or derivatives by the action of suitable agents. Optically active acids in common use for such a purpose are e.g. the D- and L-forms of tartaric acid, dibenzoyltartaric acid, ditoluoyltartaric acid, malic acid, mandelic acid, camphorsulfonic acid, glutamic acid, aspartic acid, or quinic acid. Optically active alcohols applicable as auxiliary residues may be, for example, (+) or (−)-menthol and optically active acyl groups in amides may be, for example, (+)- or (−)-menthyloxycarbonyl.

As mentioned above, the compounds of formula I may be converted into salts, particularly for pharmaceutical use into the pharmaceutically acceptable salts. As used herein, "pharmaceutically acceptable salts" refer to derivatives of the disclosed compounds wherein the parent compound is modified by making acid or base salts thereof.

The compounds according to the invention are advantageously also obtainable using the methods described in the examples that follow, which may also be combined for this purpose with methods known to the skilled man from the literature.

TERMS AND DEFINITIONS

Terms not specifically defined herein should be given the meanings that would be given to them by one of skill in the art in light of the disclosure and the context. As used in the specification, however, unless specified to the contrary, the following terms have the meaning indicated and the following conventions are adhered to.

The terms "compound(s) according to this invention", "compound(s) of formula (I)", "compound(s) of the invention" and the like denote the compounds of the formula (I) according to the present invention including their tautomers, stereoisomers and mixtures thereof and the salts thereof, in particular the pharmaceutically acceptable salts thereof, and the solvates and hydrates of such compounds, including the solvates and hydrates of such tautomers, stereoisomers and salts thereof.

The terms "treatment" and "treating" embraces both preventative, i.e. prophylactic, or therapeutic, i.e. curative and/or palliative, treatment. Thus the terms "treatment" and "treating" comprise therapeutic treatment of patients having already developed said condition, in particular in manifest form. Therapeutic treatment may be symptomatic treatment in order to relieve the symptoms of the specific indication or causal treatment in order to reverse or partially reverse the conditions of the indication or to stop or slow down progression of the disease. Thus the compositions and methods of the present invention may be used for instance as therapeutic treatment over a period of time as well as for chronic therapy. In addition the terms "treatment" and "treating" comprise prophylactic treatment, i.e. a treatment of patients at risk to develop a condition mentioned hereinbefore, thus reducing said risk.

When this invention refers to patients requiring treatment, it relates primarily to treatment in mammals, in particular humans.

The term "therapeutically effective amount" means an amount of a compound of the present invention that (i) treats or prevents the particular disease or condition, (ii) attenuates, ameliorates, or eliminates one or more symptoms of the particular disease or condition, or (iii) prevents or delays the onset of one or more symptoms of the particular disease or condition described herein.

The terms "modulated" or "modulating", or "modulate(s)", as used herein, unless otherwise indicated, refers to the activation of the G-protein-coupled receptor GPR119 with one or more compounds of the present invention.

The terms "mediated" or "mediating" or "mediate", as used herein, unless otherwise indicated, refers to the (i) treatment, including prevention of the particular disease or condition, (ii) attenuation, amelioration, or elimination of one or more symptoms of the particular disease or condition, or (iii) prevention or delay of the onset of one or more symptoms of the particular disease or condition described herein.

The term "substituted" as used herein, means that any one or more hydrogens on the designated atom, radical or moiety is replaced with a selection from the indicated group, provided that the atom's normal valence is not exceeded, and that the substitution results in an acceptably stable compound.

In the groups, radicals, or moieties defined below, the number of carbon atoms is often specified preceding the group, for example, $C_{1-6}$-alkyl means an alkyl group or radical having 1 to 6 carbon atoms. In general, for groups comprising two or more subgroups, the last named subgroup is the radical attachment point, for example, the substituent "aryl-$C_{1-3}$-alkyl-" means an aryl group which is bound to a $C_{1-3}$-alkyl-group, the latter of which is bound to the core or to the group to which the substituent is attached.

In case a compound of the present invention is depicted in form of a chemical name and as a formula in case of any discrepancy the formula shall prevail.

An asterisk may be used in sub-formulas to indicate the bond which is connected to the core molecule as defined.

The numeration of the atoms of a substituent starts with the atom which is closest to the core or to the group to which the substituent is attached.

For example, the term "3-carboxypropyl-group" represents the following substituent:

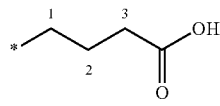

wherein the carboxy group is attached to the third carbon atom of the propyl group. The terms "1-methylpropyl-", "2,2-dimethylpropyl-" or "cyclopropylmethyl-" group represent the following groups:

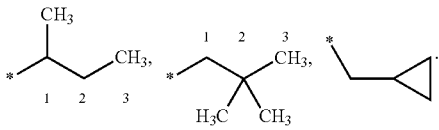

The asterisk may be used in sub-formulas to indicate the bond which is connected to the core molecule as defined.

In a definition of a group the term "wherein each X, Y and Z group is optionally substituted with" and the like denotes that each group X, each group Y and each group Z either each as a separate group or each as part of a composed group may be substituted as defined. For example a definition "$R^{ex}$ denotes H, $C_{1-3}$-alkyl, $C_{3-6}$-cycloalkyl, $C_{3-6}$-cycloalkyl-$C_{1-3}$-alkyl or $C_{1-3}$-alkyl-O—, wherein each alkyl group is optionally substituted with one or more $L^{ex}$." or the like means that in each of the beforementioned groups which comprise the term alkyl, i.e. in each of the groups $C_{1-3}$-alkyl, $C_{3-6}$-cycloalkyl-$C_{1-3}$-alkyl and $C_{1-3}$-alkyl-O—, the alkyl moiety may be substituted with $L^{ex}$ as defined.

In the following the term bicyclic includes spirocyclic.

Unless specifically indicated, throughout the specification and the appended claims, a given chemical formula or name shall encompass tautomers and all stereo, optical and geometrical isomers (e.g. enantiomers, diastereomers, E/Z isomers etc. . . . ) and racemates thereof as well as mixtures in different proportions of the separate enantiomers, mixtures of diastereomers, or mixtures of any of the foregoing forms where such isomers and enantiomers exist, as well as salts, including pharmaceutically acceptable salts thereof and solvates thereof such as for instance hydrates including solvates of the free compounds or solvates of a salt of the compound.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, and commensurate with a reasonable benefit/risk ratio.

As used herein, "pharmaceutically acceptable salts" refer to derivatives of the disclosed compounds wherein the parent compound is modified by making acid or base salts thereof.

Salts of other acids than those mentioned above which for example are useful for purifying or isolating the compounds of the present invention (e.g. trifluoro acetate salts) also comprise a part of the invention.

The term halogen generally denotes fluorine, chlorine, bromine and iodine.

The term "$C_{1-n}$-alkyl", wherein n is an integer from 1 to n, either alone or in combination with another radical denotes an acyclic, saturated, branched or linear hydrocarbon radical with 1 to n C atoms. For example the term $C_{1-5}$-alkyl embraces the radicals $H_3C$—, $H_3C$—$CH_2$—, $H_3C$—$CH_2$—$CH_2$—, $H_3C$—$CH(CH_3)$—, $H_3C$—$CH_2$—$CH_2$—$CH_2$—, $H_3C$—$CH_2$—$CH(CH_3)$—, $H_3C$—$CH(CH_3)$—$CH_2$—, $H_3C$—$C(CH_3)_2$—, $H_3C$—$CH_2$—$CH_2$—$CH_2$—$CH_2$—, $H_3C$—$CH_2$—$CH_2$—$CH(CH_3)$—, $H_3C$—$CH_2$—$CH(CH_3)$—$CH_2$—, $H_3C$—$CH(CH_3)$—$CH_2$—$CH_2$—, $H_3C$—$CH_2$—$C(CH_3)_2$—, $H_3C$—$C(CH_3)_2$—$CH_2$—, $H_3C$—$CH(CH_3)$—$CH(CH_3)$— and $H_3C$—$CH_2$—$CH(CH_2CH_3)$—.

The term "$C_{1-n}$-alkylene" wherein n is an integer 1 to n, either alone or in combination with another radical, denotes an acyclic, straight or branched chain divalent alkyl radical containing from 1 to n carbon atoms. For example the term $C_{1-4}$-alkylene includes —($CH_2$)—, —($CH_2$—$CH_2$)—, —($CH(CH_3)$)—, —($CH_2$—$CH_2$—$CH_2$)—, —($C(CH_3)_2$)—, —($CH(CH_2CH_3)$)—, —($CH(CH_3)$—$CH_2$)—, —($CH_2$—$CH(CH_3)$)—, —($CH_2$—$CH_2$—$CH_2$—$CH_2$)—, —($CH_2$—$CH_2$—$CH(CH_3)$)—, —($CH(CH_3)$—$CH_2$—$CH_2$)—, —($CH_2$—$CH(CH_3)$—$CH_2$)—, —($CH_2$—$C(CH_3)_2$)—, —($C(CH_3)_2$—$CH_2$)—, —($CH(CH_3)$—$CH(CH_3)$)—, —($CH_2$—$CH(CH_2CH_3)$)—, —($CH(CH_2CH_3)$—$CH_2$)—, —($CH(CH_2CH_2CH_3)$)—, —($CHCH(CH_3)_2$)— and —$C(CH_3)(CH_2CH_3)$—.

The term "$C_{2-n}$-alkenyl", is used for a group as defined in the definition for "$C_{1-n}$-alkyl" with at least two carbon atoms, if at least two of those carbon atoms of said group are bonded to each other by a double bond. For example the term $C_{2-3}$-alkenyl includes —CH=$CH_2$, —CH=CH—$CH_3$, —$CH_2$—CH=$CH_2$.

The term "$C_{2-n}$-alkenylene" is used for a group as defined in the definition for "$C_{1-n}$-alkylene" with at least two carbon atoms, if at least two of those carbon atoms of said group are bonded to each other by a double bond. For example the term $C_{2-3}$-alkenylene includes —CH=CH—, —CH=CH—$CH_2$—, —$CH_2$—CH=CH—.

The term "$C_{2-n}$-alkynyl", is used for a group as defined in the definition for "$C_{1-n}$-alkyl" with at least two carbon atoms, if at least two of those carbon atoms of said group are bonded to each other by a triple bond. For example the term $C_{2-3}$-alkynyl includes —C≡CH, —C≡C—$CH_3$, —$CH_2$—C≡CH.

The term "$C_{2-n}$-alkynylene" is used for a group as defined in the definition for "$C_{1-n}$-alkylene" with at least two carbon atoms, if at least two of those carbon atoms of said group are bonded to each other by a triple bond. For example the term $C_{2-3}$-alkynylene includes —C≡C—, —C≡C—$CH_2$—, —$CH_2$—C≡C—.

The term "$C_{3-n}$-carbocyclyl" as used either alone or in combination with another radical, denotes a monocyclic, bicyclic or tricyclic, saturated or unsaturated hydrocarbon radical with 3 to n C atoms. The hydrocarbon radical is preferably nonaromatic. Preferably the 3 to n C atoms form one or two rings. In case of a bicyclic or tricyclic ring system the rings may be attached to each other via a single bond or may be fused or may form a spirocyclic or bridged ring system. For example the term $C_{3-10}$-carbocyclyl includes $C_{3-10}$-cylcoalkyl, $C_{3-10}$-cycloalkenyl, octahydropentalenyl, octahydroindenyl, decahydronaphthyl, indanyl, tetrahydronaphthyl. Most preferably the term $C_{3-n}$-carbocyclyl denotes $C_{3-n}$-cylcoalkyl, in particular $C_{3-7}$-cycloalkyl.

The term "$C_{3-n}$-cycloalkyl", wherein n is an integer from 4 to n, either alone or in combination with another radical denotes a cyclic, saturated, unbranched hydrocarbon radical with 3 to n C atoms. The cyclic group may be mono-, bi-, tri- or spirocyclic, most preferably monocyclic. Examples of such cycloalkyl groups include cyclopropyl, cyclobutyl, cyclopentyl, cyclohexyl, cycloheptyl, cyclooctyl, cyclononyl, cyclododecyl, bicyclo[3.2.1]octyl, spiro[4.5]decyl, norpinyl, norbonyl, norcaryl, adamantyl, etc.

The term "$C_{3-n}$-cycloalkenyl", wherein n is an integer from 4 to n, either alone or in combination with another radical, denotes a cyclic, unsaturated but nonaromatic, unbranched hydrocarbon radical with 3 to n C atoms, at least two of which are bonded to each other by a double bond. For example the term $C_{3-7}$-cycloalkenyl includes cyclopropenyl, cyclobutenyl, cyclopentenyl, cyclopentadienyl, cyclohexenyl, cyclohexadienyl, cycloheptenyl, cycloheptadienyl and cycloheptatrienyl.

The term "aryl" as used herein, either alone or in combination with another radical, denotes a carbocyclic aromatic monocyclic group containing 6 carbon atoms which may be further fused to a second 5- or 6-membered carbocyclic group which may be aromatic, saturated or unsaturated. Aryl includes, but is not limited to, phenyl, indanyl, indenyl, naphthyl, anthracenyl, phenanthrenyl, tetrahydronaphthyl and dihydronaphthyl. More preferably the term "aryl" as used herein, either alone or in combination with another radical, denotes phenyl or naphthyl, most preferably phenyl.

The term "heterocyclyl" means a saturated or unsaturated mono-, bi-, tri- or spirocarbocyclic, preferably mono-, bi- or spirocyclic-ring system containing one or more heteroatoms selected from N, O or S(O)$_r$ with r=0, 1 or 2, which in addition may have a carbonyl group. More preferably the term "heterocyclyl" as used herein, either alone or in combination with another radical, means a saturated or unsaturated, even more preferably a saturated mono-, bi- or spirocyclic-ring system containing 1, 2, 3 or 4 heteroatoms selected from N, O or S(O)$_r$ with r=0, 1 or 2 which in addition may have a carbonyl group. The term "heterocyclyl" is intended to include all the possible isomeric forms. Examples of such groups include aziridinyl, oxiranyl, azetidinyl, oxetanyl, pyrrolidinyl, tetrahydrofuranyl, piperidinyl, tetrahydropyranyl, azepanyl, piperazinyl, morpholinyl, tetrahydrofuranonyl, tetrahydropyranonyl, pyrrolidinonyl, piperidinonyl, piperazinonyl, and morpholinonyl.

Thus, the term "heterocyclyl" includes the following exemplary structures which are not depicted as radicals as each form may be attached through a covalent bond to any atom so long as appropriate valences are maintained:

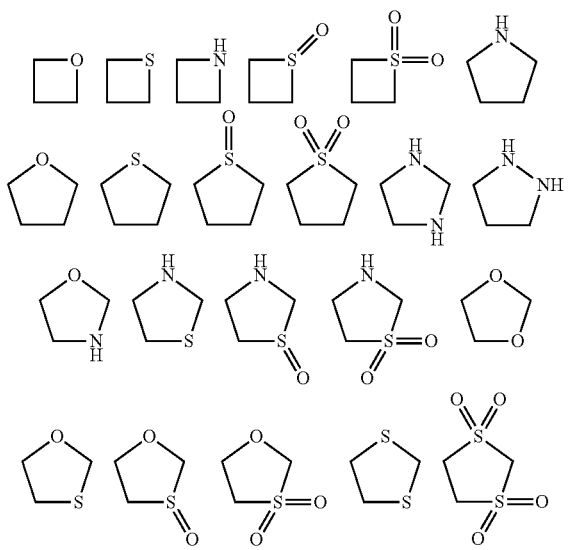

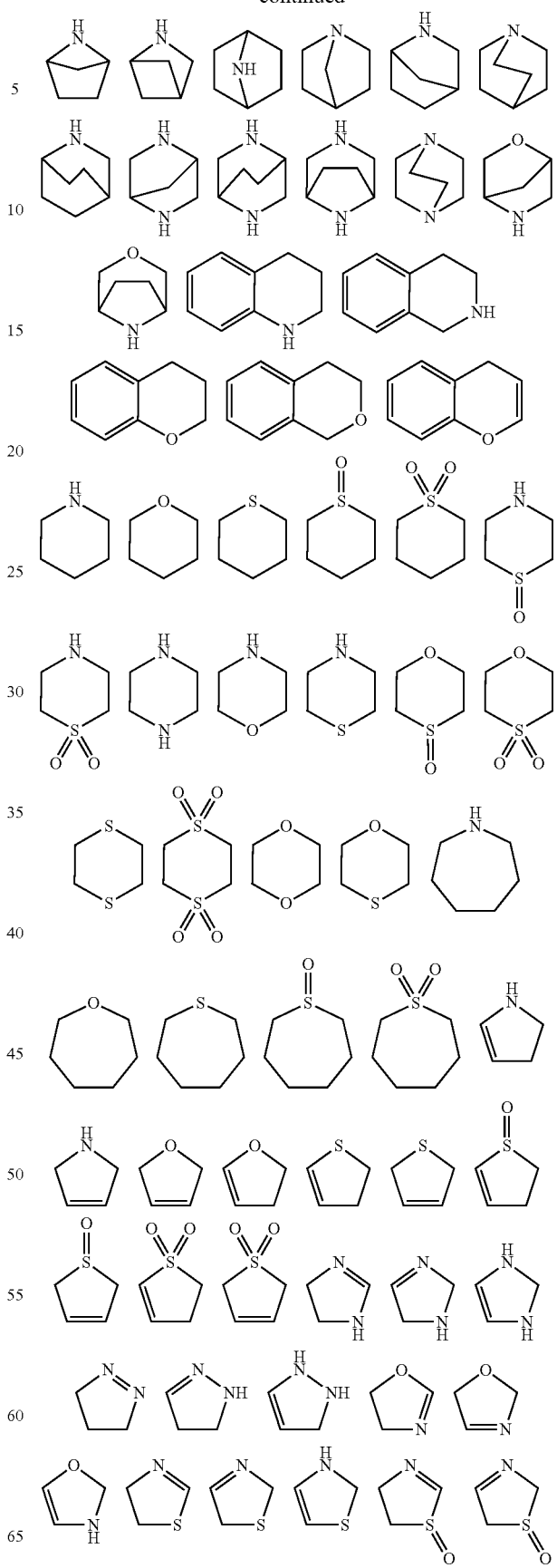

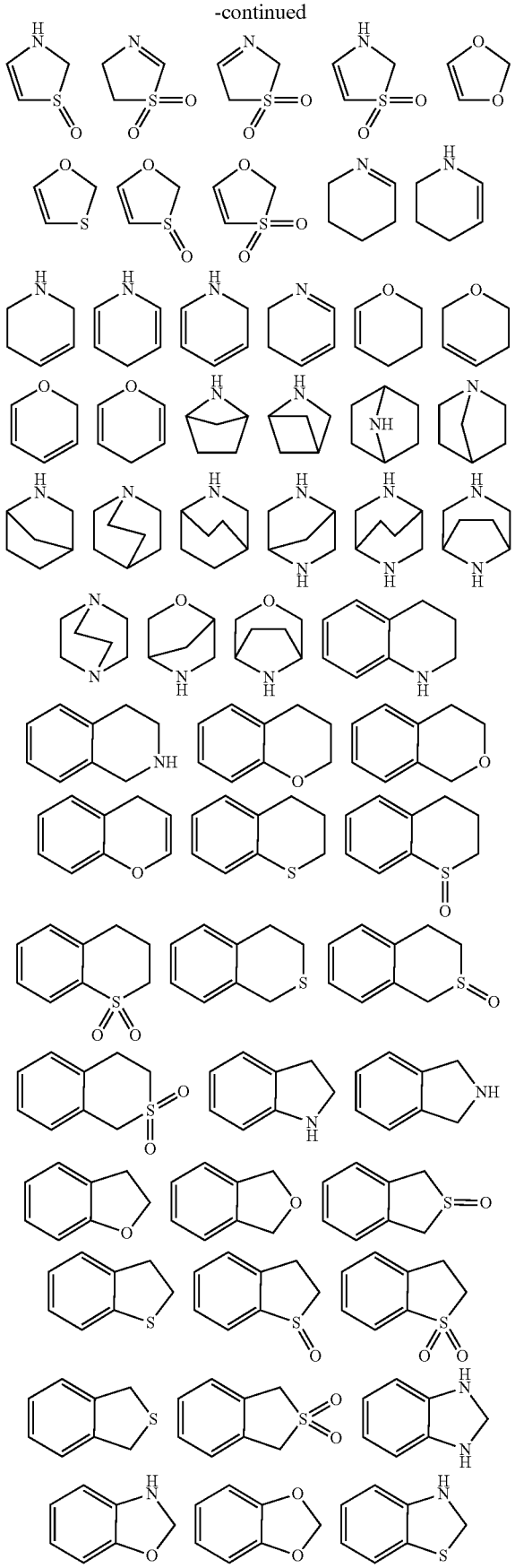
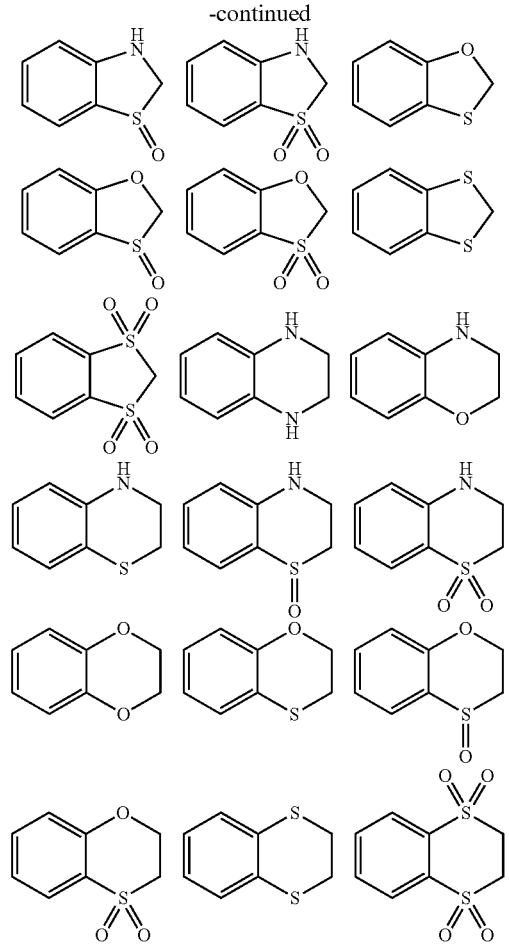

The term "heteroaryl" means a mono- or polycyclic, preferably mono- or bicyclic ring system containing one or more heteroatoms selected from N, O or S(O)$_r$ with r=0, 1 or 2 wherein at least one of the heteroatoms is part of an aromatic ring, and wherein said ring system may have a carbonyl group. More preferably the term "heteroaryl" as used herein, either alone or in combination with another radical, means a mono- or bicyclic-ring system containing 1, 2, 3 or 4 heteroatoms selected from N, O or S(O)$_r$ with r=0, 1 or 2 wherein at least one of the heteroatoms is part of an aromatic ring, and wherein said ring system may have a carbonyl group. The term "heteroaryl" is intended to include all the possible isomeric forms.

Thus, the term "heteroaryl" includes the following exemplary structures which are not depicted as radicals as each form may be attached through a covalent bond to any atom so long as appropriate valences are maintained:

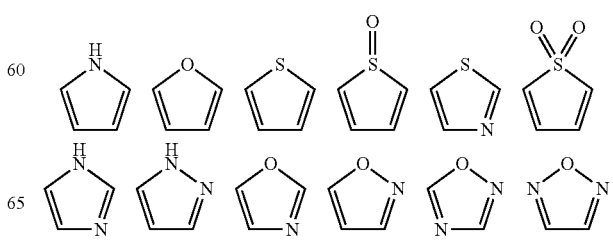

-continued

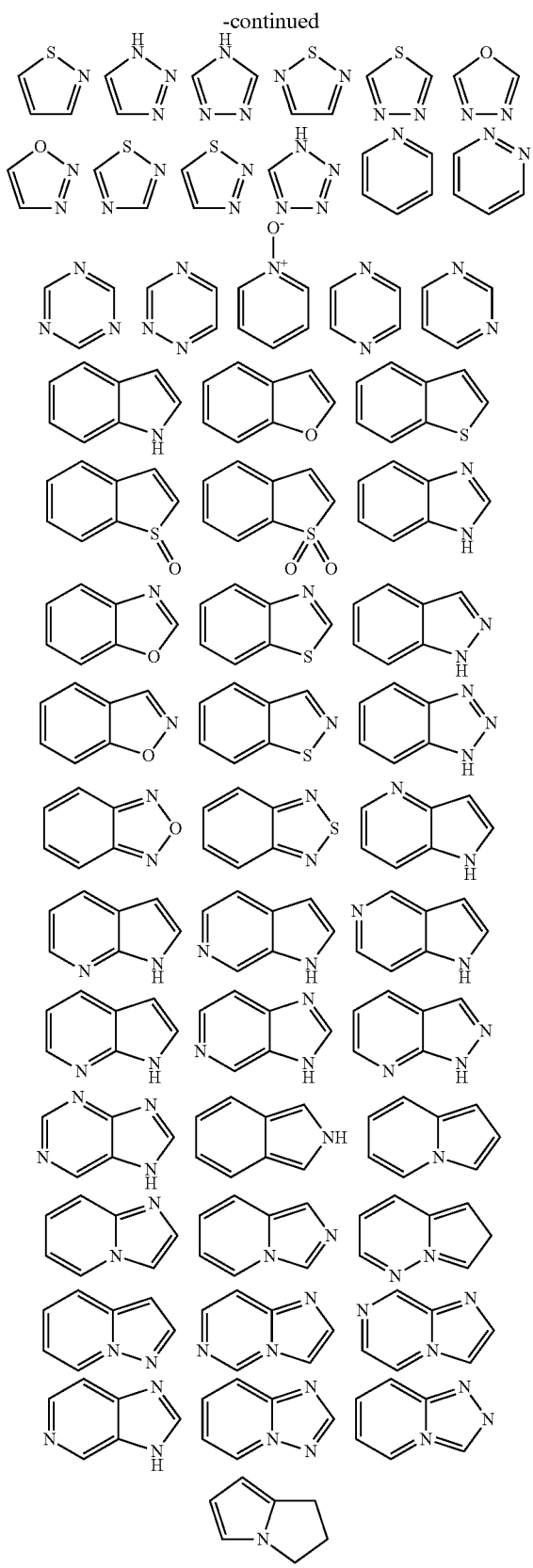

Many of the terms given above may be used repeatedly in the definition of a formula or group and in each case have one of the meanings given above, independently of one another.

Pharmacological Activity

The activity of the compounds of the invention may be demonstrated using the following assay:

The compounds of formula I according to the invention modulate the activity of the G-protein-coupled receptor GPR119. The effect of the compounds on the activation of GPR119 and on the stimulation of intracellular cAMP concentration is determined using the AlphaScreen cAMP Assay Kit (Cat. No. #6760625R) made by PerkinElmer.

MIN6 cells [Miyazaki J et al. Endocrinology. 1990 July; 127(1):126-32] are stably transfected with an expression vector for human GPR119 cDNA (Acc. No. NP_848566). Min-6/hGPR119 cells are cultured in DMEM, 10% FBS, 50 µM β-mercaptoethanol, 0.3 mg/mL Geniticin, 2 mM GlutaMAX at 37° C. 5% $CO_2$. For the assay, the cells are seeded in Optiplates (white, 384-well, 160W-barcoded, TC, sterile with lid, Cat. No. #6007688 (Perkin Elmer); 10000 cells/well; 50 µl). The plates covered with lids are then incubated for 24 hours at 37° C./5% $CO_2$. After the medium is aspirated from the wells completely, 10 µl of the test compound are added, the compounds are diluted using stimulating buffer (140 mM NaCl, 3.6 mM KCl, 0.5 mM $NaH_2PO_4$, 0.5 mM $MgSO_4$, 1.5 mM $CaCl_2$, 10 mM Hepes, 5 mM $NaHCO_3$; pH 7.4. 0.5 mM IBMX and 0.1% BSA, the final DMSO concentration is 1%). After 45 minutes incubation at room temperature (approx. 20° C.), the cAMP concentrations are determined using the AlphaScreen cAMP Assay Kit (Cat. No. #6760625R from PerkinElmer). 10 µl of Biotin-cAMP (final concentration 1 U/well in lysing buffer (5 mM Hepes (pH 7.4), 0.1% BSA, 0.5% Tween) and 10 µL Bead solution (final concentration 1 U/well in lysing buffer) are added. The plates are incubated for another 2 hours at room temperature. The cAMP concentrations are calculated using a cAMP standard curve from the Alpha Screen Counts. The data analysis is carried out by calculating the EC50 value and the maximum value based on a positive control, using suitable software (Graphpad Prism). The compounds according to the invention increase the intracellular cAMP level in the range of 3-5.

The compounds according to the invention typically have $EC_{50}$ values in the range from about 1 nM to about 10 µM, preferably less than 1 µM, more preferably less than 500 nM, most preferably less than 100 nM.

$EC_{50}$ values for compounds according to the invention are shown in the following Table. The number of the compound corresponds to the number of the Example in the experimental section.

| Example | $EC_{50}$ [nM] | Example | $EC_{50}$ [nM] | Example | $EC_{50}$ [nM] | Example | $EC_{50}$ [nM] |
|---|---|---|---|---|---|---|---|
| 1 | 417 | 2 | 25 | 3 | 36 | 4 | 215 |
| 5 | 663 | 6 | 21 | 7 | 22 | 8 | 35 |
| 9 | 100 | 10 | 66 | 11 | 848 | 12 | 46 |
| 13 | 5 | 14 | 2 | 15 | 78 | 16 | 25 |
| 17 | 25 | 18 | 27 | 19 | 84 | | |

In view of their ability to modulate the activity of the G-protein-coupled receptor GPR119, in particular an agonistic activity, the compounds of general formula (I) according to the invention, including the corresponding salts thereof, are theoretically suitable for the treatment of all those diseases or conditions which may be affected or which are mediated by the activation of the G-protein-coupled receptor GPR119.

Accordingly, the present invention relates to a compound of general formula (I) as a medicament.

Furthermore, the present invention relates to the use of a compound of general formula (I) or a pharmaceutical composition according to this invention for the treatment and/or prevention of diseases or conditions which are mediated by the activation of the G-protein-coupled receptor GPR119 in a patient, preferably in a human.

In yet another aspect the present invention relates to a method for treating a disease or condition mediated by the activation of the G-protein-coupled receptor GPR119 in a mammal that includes the step of administering to a patient, preferably a human, in need of such treatment a therapeutically effective amount of a compound or a pharmaceutical composition of the present invention.

Diseases and conditions mediated by agonists of the G-protein-coupled receptor GPR119 embrace metabolic diseases or conditions.

According to one aspect the compounds and pharmaceutical compositions of the present invention are particularly suitable for treating diabetes mellitus, in particular Type 2 diabetes, Type 1 diabetes, complications of diabetes (such as e.g. retinopathy, nephropathy or neuropathies, diabetic foot, ulcers or macroangiopathies), metabolic acidosis or ketosis, reactive hypoglycaemia, hyperinsulinaemia, glucose metabolic disorder, insulin resistance, metabolic syndrome, dyslipidaemias of different origins, atherosclerosis and related diseases, obesity, high blood pressure, chronic heart failure, oedema and hyperuricaemia.

The compounds and pharmaceutical compositions of the present invention are also suitable for preventing beta-cell degeneration such as e.g. apoptosis or necrosis of pancreatic beta cells. The compounds and pharmaceutical compositions of the present invention are also suitable for improving or restoring the functionality of pancreatic cells, and also for increasing the number and size of pancreatic beta cells.

Therefore according to another aspect the invention relates to compounds of formula I and pharmaceutical compositions according to the invention for use in preventing, delaying, slowing the progression of and/or treating metabolic diseases, particularly in improving the glycaemic control and/or beta cell function in the patient.

In another aspect the invention relates to compounds of formula I and pharmaceutical compositions according to the invention for use in preventing, delaying, slowing the progression of and/or treating type 2 diabetes, overweight, obesity, complications of diabetes and associated pathological conditions.

In addition the compounds and pharmaceutical compositions according to the invention are suitable for use in one or more of the following therapeutic processes:

for preventing, delaying, slowing the progression of or treating metabolic diseases, such as for example type 1 diabetes, type 2 diabetes, insufficient glucose tolerance, insulin resistance, hyperglycaemia, hyperlipidaemia, hypercholesterolaemia, dyslipidaemia, syndrome X, metabolic syndrome, obesity, high blood pressure, chronic systemic inflammation, retinopathy, neuropathy, nephropathy, atherosclerosis, endothelial dysfunction or bone-related diseases (such as osteoporosis, rheumatoid arthritis or osteoarthritis);

for improving glycaemic control and/or reducing fasting plasma glucose, postprandial plasma glucose and/or the glycosylated haemoglobin HbA1c;

for preventing, delaying, slowing or reversing the progression of disrupted glucose tolerance, insulin resistance and/or metabolic syndrome to type 2 diabetes;

for preventing, delaying, slowing the progression of or treating a condition or a disease selected from among the complications of diabetes, such as for example retinopathy, nephropathy or neuropathies, diabetic foot, ulcers or macroangiopathies;

for reducing weight or preventing weight gain or assisting weight loss;

for preventing or treating the degradation of pancreatic beta cells and/or improving and/or restoring the functionality of pancreatic beta cells and/or restoring the functionality of pancreatic insulin secretion;

for maintaining and/or improving insulin sensitivity and/or preventing or treating hyperinsulinaemia and/or insulin resistance.

In particular, the compounds and pharmaceutical compositions according to the invention are suitable for the treatment of obesity, diabetes (comprising type 1 and type 2 diabetes, preferably type 2 diabetes mellitus) and/or complications of diabetes (such as for example retinopathy, nephropathy or neuropathies, diabetic foot, ulcers or macroangiopathies).

The compounds according to the invention are most particularly suitable for treating type 2 diabetes mellitus.

The dose range of the compounds of general formula (I) applicable per day is usually from 0.001 to 10 mg per kg body weight, for example from 0.01 to 8 mg per kg body weight of the patient. Each dosage unit may conveniently contain from 0.1 to 1000 mg, for example 0.5 to 500 mg.

The actual therapeutically effective amount or therapeutic dosage will of course depend on factors known by those skilled in the art such as age and weight of the patient, route of administration and severity of disease. In any case the compound or composition will be administered at dosages and in a manner which allows a therapeutically effective amount to be delivered based upon patient's unique condition.

The compounds, compositions, including any combinations with one or more additional therapeutic agents, according to the invention may be administered by oral, transdermal, inhalative, parenteral or sublingual route. Of the possible methods of administration, oral or intravenous administration is preferred.

Pharmaceutical Compositions

Suitable preparations for administering the compounds of formula (I), optionally in combination with one or more further therapeutic agents, will be apparent to those with ordinary skill in the art and include for example tablets, pills, capsules, suppositories, lozenges, troches, solutions, syrups, elixirs, sachets, injectables, inhalatives and powders etc. Oral formulations, particularly solid forms such as e.g. tablets or capsules are preferred. The content of the pharmaceutically active compound(s) is advantageously in the range from 0.1 to 90 wt.-%, for example from 1 to 70 wt.-% of the composition as a whole.

Suitable tablets may be obtained, for example, by mixing one or more compounds according to formula (I) with known excipients, for example inert diluents, carriers, disintegrants, adjuvants, surfactants, binders and/or lubricants. The tablets may also consist of several layers. The particular excipients, carriers and/or diluents that are suitable for the desired preparations will be familiar to the skilled man on the basis of his specialist knowledge. The preferred ones are those that are suitable for the particular formulation and method of administration that are desired. The preparations or formulations according to the invention may be prepared using methods known per se that are familiar to the skilled man, such as for example by mixing or combining at least one compound of formula I according to the invention, or a pharmaceutically acceptable salt of such a compound, and one or more excipients, carriers and/or diluents.

Combination Therapy

The compounds of the invention may further be combined with one or more, preferably one additional therapeutic agent. According to one embodiment the additional therapeutic agent is selected from the group of therapeutic agents useful in the treatment of diseases or conditions described hereinbefore, in particular associated with metabolic diseases or conditions such as for example diabetes mellitus, obesity, diabetic complications, hypertension, hyperlipidemia. Additional therapeutic agents which are suitable for such combinations include in particular those which for example potentiate the therapeutic effect of one or more active substances with respect to one of the indications mentioned and/or which allow the dosage of one or more active substances to be reduced.

Therefore a compound of the invention may be combined with one or more additional therapeutic agents selected from the group consisting of antidiabetic agents, agents for the treatment of overweight and/or obesity and agents for the treatment of high blood pressure, heart failure and/or atherosclerosis.

Antidiabetic agents are for example metformin, sulphonylureas, nateglinide, repaglinide, thiazolidinediones, PPAR-(alpha, gamma or alpha/gamma) agonists or modulators, alpha-glucosidase inhibitors, DPPIV inhibitors, SGLT2-inhibitors, insulin and insulin analogues, GLP-1 and GLP-1 analogues or amylin and amylin analogues, cycloset, 11β-HSD inhibitors. Other suitable combination partners are inhibitors of protein tyrosinephosphatase 1, substances that affect deregulated glucose production in the liver, such as e.g. inhibitors of glucose-6-phosphatase, or fructose-1,6-bisphosphatase, glycogen phosphorylase, glucagon receptor antagonists and inhibitors of phosphenol pyruvate carboxykinase, glycogen synthase kinase or pyruvate dehydrokinase, alpha2-antagonists, CCR-2 antagonists or glucokinase activators. One or more lipid lowering agents are also suitable as combination partners, such as for example HMG-CoA-reductase inhibitors, fibrates, nicotinic acid and the derivatives thereof, PPAR-(alpha, gamma or alpha/gamma) agonists or modulators, PPAR-delta agonists, ACAT inhibitors or cholesterol absorption inhibitors such as, bile acid-binding substances such as, inhibitors of ileac bile acid transport, MTP inhibitors, or HDL-raising compounds such as CETP inhibitors or ABC1 regulators.

Therapeutic agents for the treatment of overweight and/or obesity are for example antagonists of the cannabinoid1 receptor, MCH-1 receptor antagonists, MC4 receptor agonists, NPY5 or NPY2 antagonists, β3-agonists, leptin or leptin mimetics, agonists of the 5HT2c receptor.

Therapeutic agents for the treatment of high blood pressure, chronic heart failure and/or atherosclerosis are for example A-II antagonists or ACE inhibitors, ECE inhibitors, diuretics, β-blockers, Ca-antagonists, centrally acting antihypertensives, antagonists of the alpha-2-adrenergic receptor, inhibitors of neutral endopeptidase, thrombocyte aggregation inhibitors and others or combinations thereof are suitable. Angiotensin II receptor antagonists are preferably used for the treatment or prevention of high blood pressure and complications of diabetes, often combined with a diuretic such as hydrochlorothiazide.

The dosage for the combination partners mentioned above is usually ⅕ of the lowest dose normally recommended up to 1/1 of the normally recommended dose.

Preferably, compounds of the present invention and/or pharmaceutical compositions comprising a compound of the present invention optionally in combination with one or more additional therapeutic agents are administered in conjunction with exercise and/or a diet.

Therefore, in another aspect, this invention relates to the use of a compound according to the invention in combination with one or more additional therapeutic agents described hereinbefore and hereinafter for the treatment of diseases or conditions which may be affected or which are mediated by the activation of the G-protein-coupled receptor GPR119, in particular diseases or conditions as described hereinbefore and hereinafter.

In yet another aspect the present invention relates a method for treating a disease or condition mediated by the activation of the G-protein-coupled receptor GPR119 in a patient that includes the step of administering to the patient, preferably a human, in need of such treatment a therapeutically effective amount of a compound of the present invention in combination with a therapeutically effective amount of one or more additional therapeutic agents described in hereinbefore and hereinafter.

The use of the compound according to the invention in combination with the additional therapeutic agent may take place simultaneously or at staggered times.

The compound according to the invention and the one or more additional therapeutic agents may both be present together in one formulation, for example a tablet or capsule, or separately in two identical or different formulations, for example as a so-called kit-of-parts.

Consequently, in another aspect, this invention relates to a pharmaceutical composition which comprises a compound according to the invention and one or more additional therapeutic agents described hereinbefore and hereinafter, optionally together with one or more inert carriers and/or diluents.

Other features and advantages of the present invention will become apparent from the following more detailed Examples which illustrate, by way of example, the principles of the invention.

EXAMPLES

The terms "ambient temperature" and "room temperature" are used interchangeably and designate a temperature of about 20° C.

Preliminary Remarks:

As a rule, $^1$H-NMR and/or mass spectra have been obtained for the compounds prepared. The $R_f$ values are determined using Merck silica gel 60 $F_{254}$ plates and UV light at 254 nm or staining with phosphomolybdic acid.

Analytical HPLC parameters employed for characterization of products (TFA denotes trifluoroacetic acid):

| method 1 column | Waters XBridge C18, 4.6 × 30 mm, 3.5 μm | | |
|---|---|---|---|
| mobile phase | A: water + 0.1% formic acid | | |
| | B: methanol | | |
| | TIME (min) | A % | B % |
| | 0.0 | 95 | 5 |
| | 0.15 | 95 | 5 |
| | 1.70 | 0 | 100 |
| | 2.25 | 0 | 100 |
| flow rate | 4.0 mL/min | | |
| wavelength | UV 220, 230, or 254 nm | | |
| method 2 column | Waters XBridge C18, 3 × 30 mm, 2.5 μm | | |
| mobile phase | A: water + 0.1% NH$_4$OH | | |
| | B: methanol | | |

| TIME (min) | A % | B % |
| --- | --- | --- |
| 0.0 | 95 | 5 |
| 0.05 | 95 | 5 |
| 1.40 | 0 | 100 |
| 1.80 | 0 | 100 |

| flow rate | 2.2 mL/min |
| --- | --- |
| wavelength | UV 220, 230, or 254 nm |
| method 3 column | Waters XBridge C18, 4.6 × 30 mm, 3.5 μm |
| mobile phase | A: water + 0.1% TFA |
| | B: methanol |

| TIME (min) | A % | B % |
| --- | --- | --- |
| 0.0 | 95 | 5 |
| 1.60 | 0 | 100 |
| 1.85 | 0 | 100 |
| 1.90 | 95 | 5 |

| flow rate | 4.0 mL/min |
| --- | --- |
| wavelength | UV 220, 230, or 254 nm |
| method 4 column | Waters XBridge C18, 3 × 30 mm, 2.5 μm |
| mobile phase | A: water + 0.1% TFA |
| | B: methanol |

| TIME (min) | A % | B % |
| --- | --- | --- |
| 0.0 | 95 | 5 |
| 0.05 | 95 | 5 |
| 1.40 | 0 | 100 |
| 1.80 | 0 | 100 |

| flow rate | 2.2 mL/min |
| --- | --- |
| wavelength | UV 220, 230, or 254 nm |

Intermediate 1

4-(5-Bromo-2-hydroxy-phenylethynyl)-piperidine-1-carboxylic acid tert-butyl ester

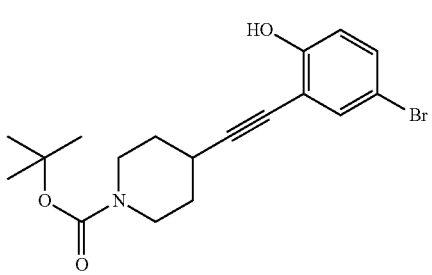 [SMILES: CC(C)(C)OC(=O)N1CCC(C#Cc2cc(Br)ccc2O)CC1]

A mixture of 4-ethynyl-piperidine-1-carboxylic acid tert-butyl ester (4.03 g), 4-bromo-2-iodo-phenol (5.00 g), Pd(PPh$_3$)$_2$Cl$_2$ (600 mg), copper iodide (500 mg), and triethylamine (2.35 mL) in N,N-dimethylformamide (30 mL) is heated under an argon atmosphere to 75° C. for 4 h. The reaction mixture is diluted with ice water after cooling to room temperature and extracted with ethyl acetate. The combined extracts are dried over MgSO$_4$ and concentrated in vacuo. The residue is chromatographed on silica gel (cyclohexane/ethyl acetate 80:20→60:40) to give the title compound. LC (method 2): t$_R$=1.32 min; Mass spectrum (ESI$^+$): m/z=402, 404 [M+Na]$^+$.

Intermediate 2

4-(5-Bromo-benzofuran-2-yl)-piperidine-1-carboxylic acid tert-butyl ester

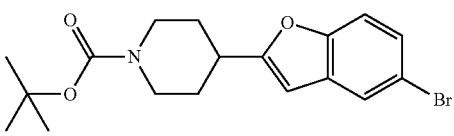 [SMILES: CC(C)(C)OC(=O)N1CCC(c2cc3cc(Br)ccc3o2)CC1]

A mixture of 4-(5-bromo-2-hydroxy-phenylethynyl)-piperidine-1-carboxylic acid tert-butyl ester (70 mg), copper iodide (9 mg), N,N-dimethylformamide (1 mL), triethylamine (100 μL), and Pd(PPh$_3$)$_2$Cl$_2$ (7 mg) is heated under an argon atmosphere to 55° C. for 0.5 h. The reaction mixture is diluted with ice water after cooling to room temperature and extracted with ethyl acetate. The combined extracts are dried over MgSO$_4$ and concentrated in vacuo. The residue is chromatographed on silica gel (cyclohexane/ethyl acetate 80:20→50:50) to give the title compound. LC (method 2): t$_R$=1.49 min; Mass spectrum (ESI$^+$): m/z=380, 382 [M+H]$^+$.

Intermediate 3

4-[5-(4-Methanesulfonyl-phenyl)-benzofuran-2-yl]-piperidine-1-carboxylic acid tert-butyl ester

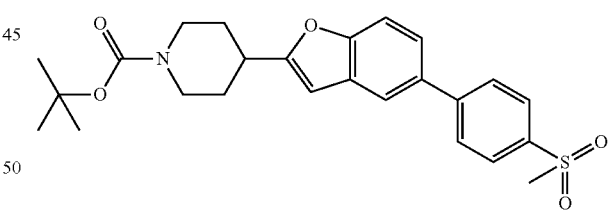

An aqueous Na$_2$CO$_3$ solution (2 M, 0.68 mL) is added to a mixture of 4-(5-bromo-benzofuran-2-yl)-piperidine-1-carboxylic acid tert-butyl ester (2.50 g) and 4-(methanesulfonyl)phenylboronic acid (1.97 g) in a mixture of dioxane/water (60:40). The mixture is sparged with argon for 10 min and PdCl$_2$[1,1'-bis(diphenylphosphino)-ferrocene]*CH$_2$Cl$_2$ complex (500 mg) is added. The resulting mixture is heated to 100° C. for 2 h. After cooling to room temperature, ethyl acetate, brine, and activated charcoal are added. The mixture is filtered and the organic phase is separated, dried over Na$_2$SO$_4$, and the solvent is evaporated. The residue is chromatographed on silica gel (cyclohexane/ethyl acetate 80:20→60:40) to give the title compound. LC (method 1): t$_R$=1.80 min; Mass spectrum (ESI$^+$): m/z=478 [M+Na]$^+$.

Intermediate 4

4-[5-(4-Methanesulfonyl-phenyl)-2,3-dihydro-benzofuran-2-yl]-piperidine-1-carboxylic acid tert-butyl ester

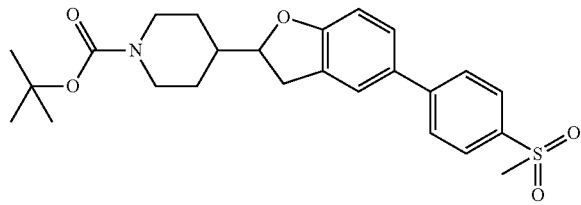 [SMILES: CC(C)(C)OC(=O)N1CCC(C2Cc3cc(-c4ccc(S(C)(=O)=O)cc4)ccc3O2)CC1]

A mixture of 4-[5-(4-methanesulfonyl-phenyl)-benzofuran-2-yl]-piperidine-1-carboxylic acid tert-butyl ester (1.70 g), 10% palladium on carbon (200 mg), ethanol (100 mL), and ethyl acetate (50 mL) is shaken under hydrogen atmosphere (5 bar) at 45° C. until the starting material is completely consumed. The catalyst is filtered off, the filtrate is concentrated in vacuo, and the residue is chromatographed on silica gel (cyclohexane/ethyl acetate/methanol 70:30:0→50:40:10) to give the title compound. LC (method 1): $t_R$=1.75 min; Mass spectrum (ESI$^+$): m/z=458 [M+H]$^+$.

Intermediate 5

4-[5-(4-Methanesulfonyl-phenyl)-2,3-dihydro-benzofuran-2-yl]-piperidine

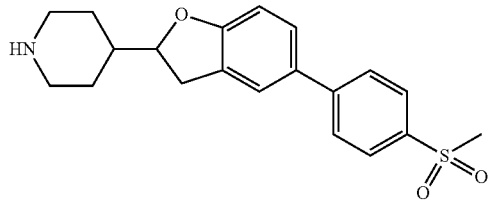 [SMILES: CS(=O)(=O)c1ccc(-c2ccc3c(c2)CC(C2CCNCC2)O3)cc1]

A solution of HCl in dioxane (4 N, 5.0 mL) is added to 4-[5-(4-methanesulfonyl-phenyl)-2,3-dihydro-benzofuran-2-yl]-piperidine-1-carboxylic acid tert-butyl ester (750 mg) in dichloromethane (1 mL) and the resulting mixture is stirred for 5 min at room temperature. The solvents are evaporated in vacuo to give the title compound as its hydrochloric acid salt. Mass spectrum (ESI$^+$): m/z=358 [M+H]$^+$.

Intermediate 6

1-{-4-[5-(4-Methanesulfonyl-phenyl)-2,3-dihydro-benzofuran-2-yl]-piperidin-1-yl}-2-methyl-propan-2-ol

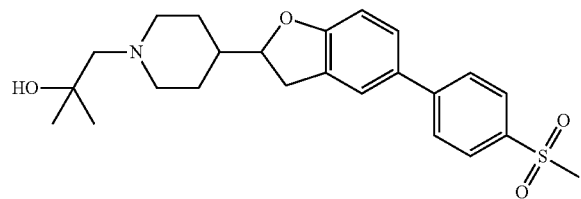

A mixture of 4-[5-(4-methanesulfonyl-phenyl)-2,3-dihydro-benzofuran-2-yl]-piperidine hydrochloride (100 mg) and N,N-diisopropylethylamine (46 µl) in methanol (5 mL) is stirred for 10 min at room temperature. 1,1-Dimethyloxirane (34 µl) is added and the resulting mixture is heated to 45° C. After the conversion is complete, the solvents are evaporated in vacuo and the crude product is used for the next step without further purification. LC (method 1): $t_R$=1.09 min; Mass spectrum (ESI$^+$): m/z=430 [M+H]$^+$.

Intermediate 7

4-[2-(5-Bromo-2-chloro-pyridin-4-yl)-acetyl]-piperidine-1-carboxylic acid tert-butyl ester

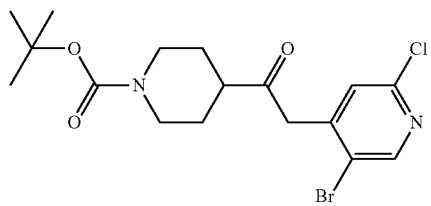 [SMILES: CC(C)(C)OC(=O)N1CCC(C(=O)Cc2cc(Cl)ncc2Br)CC1]

Lithium bis(trimethylsilyl)amide solution (1.0 M in tetrahydrofuran; 11.00 mL) is added dropwise to 5-bromo-2-chloro-4-picoline (950 mg) in tetrahydrofuran (15 mL) at −40° C. under argon atmosphere. The mixture is stirred for 2 h at −35° C. to −45° C. prior to the addition of piperidine-1,4-dicarboxylic acid 1-tert-butyl ester 4-ethyl ester (1.33 g) dissolved in tetrahydrofuran (15 mL). The reaction mixture is allowed to warm to room temperature over a period of 1 h. Ice-cold water is added and the mixture is extracted with ethyl acetate. The combined extracts are washed with brine, dried over MgSO$_4$, and concentrated in vacuo. The residue is chromatographed on silica gel (cyclohexane/ethyl acetate 75:25→60:40) to give the title compound. LC (method 3): $t_R$=1.43 min; Mass spectrum (ESI$^+$): m/z=417, 419 [M+H]$^+$.

Intermediate 8

4-[2-(5-Bromo-2-chloro-pyridin-4-yl)-1-hydroxy-ethyl]-piperidine-1-carboxylic acid tert-butyl ester

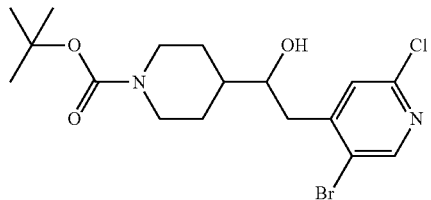 [SMILES: CC(C)(C)OC(=O)N1CCC(C(O)Cc2cc(Cl)ncc2Br)CC1]

Sodium borohydride (240 mg) is added to an ice-cooled solution of 4-[2-(5-bromo-2-chloro-pyridin-4-yl)-acetyl]-piperidine-1-carboxylic acid tert-butyl ester (1.65 g) in a mixture of tetrahydrofuran (40 mL) and water (10 mL). The resulting mixture is stirred for 0.5 h at room temperature. 2 N Aqueous citric acid is added and the mixture is extracted with ethyl acetate. The combined extracts are washed with aqueous NaHCO$_3$ solution and brine, dried over MgSO$_4$, and concentrated in vacuo. The residue is chromatographed on silica gel (cyclohexane/ethyl acetate 65:35) to give the title compound. LC (method 3): $t_R$=1.48 min; Mass spectrum (ESI$^+$): m/z=419, 421 [M+H]$^+$.

Intermediate 9

4-(5-Chloro-2,3-dihydro-furo[2,3-c]pyridin-2-yl)-piperidine-1-carboxylic acid tert-butyl ester

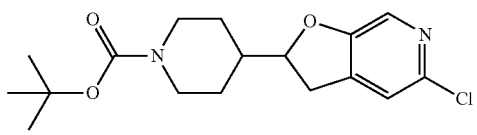 [SMILES: CC(C)(C)OC(=O)N1CCC(C2Cc3cc(Cl)ncc3O2)CC1]

A mixture of 4-[2-(5-bromo-2-chloro-pyridin-4-yl)-1-hydroxy-ethyl]-piperidine-1-carboxylic acid tert-butyl ester (11.60 g), palladium acetate (500 mg), racemic 2-(di-tert-butylphosphino)-1,1'-binaphthyl (1.00 g), and cesium carbonate (14.00 g) in toluene (150 mL) is heated in an oil bath at 110° C. under argon atmosphere for 5 h. After cooling to room temperature, ethyl acetate and water are added and the organic phase is separated, washed with brine, dried over MgSO$_4$, and concentrated in vacuo. The residue is chromatographed on silica gel (cyclohexane/ethyl acetate 70:30→50:50) to give the title compound. LC (method 3): t$_R$=1.44 min; Mass spectrum (ESI$^+$): m/z=339 [M+H]$^+$.

Intermediate 10

4-[5-(4-Methanesulfonyl-phenyl)-2,3-dihydro-furo[2,3-c]pyridin-2-yl]-piperidine-1-carboxylic acid tert-butyl ester

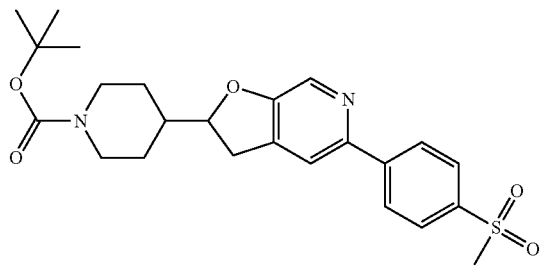

A mixture of 4-(5-chloro-2,3-dihydro-furo[2,3-c]pyridin-2-yl)-piperidine-1-carboxylic acid tert-butyl ester (400 mg), 4-(methanesulfonyl)phenyl boronic acid (321 mg), aqueous Na$_2$CO$_3$ solution (2 M; 1.60 mL), and dioxane (15 mL) is sparged with argon for 10 min and Pd(PPh$_3$)$_4$ (100 mg) is added. The resulting mixture is heated to 150° C. in a microwave oven until the conversion is complete. The reaction mixture is diluted with water and extracted with ethyl acetate. The organic phase is dried over MgSO$_4$ and the solvent is evaporated. The residue is chromatographed on silica gel (cyclohexane/ethyl acetate 40:60→20:80) to give the title compound. LC (method 3): t$_R$=1.32 min; Mass spectrum (ESI$^+$): m/z=459 [M+H]$^+$.

Intermediate 11

5-(4-Methanesulfonyl-phenyl)-2-piperidin-4-yl-2,3-dihydro-furo[2,3-c]pyridine

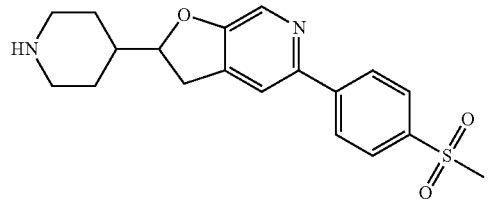

A mixture of 4-[5-(4-methanesulfonyl-phenyl)-2,3-dihydro-furo[2,3-c]pyridin-2-yl]-piperidine-1-carboxylic acid tert-butyl ester (190 mg) and trifluoroacetic acid (0.40 mL) in dichloromethane (3 mL) is stirred at room temperature for 2 h. The reaction mixture is diluted with dichloromethane and washed with aqueous Na$_2$CO$_3$ solution. The aqueous phase is extracted with dichloromethane and the combined organic phases are washed with water, dried over MgSO$_4$, and concentrated in vacuo. LC (method 3): t$_R$=0.62 min; Mass spectrum (ESI$^+$): m/z=359 [M+H]$^+$.

Intermediate 12

4-[5-(1-Methanesulfonyl-1,2,3,6-tetrahydro-pyridin-4-yl)-2,3-dihydro-furo[2,3-c]pyridin-2-yl]-piperidine-1-carboxylic acid tert-butyl ester

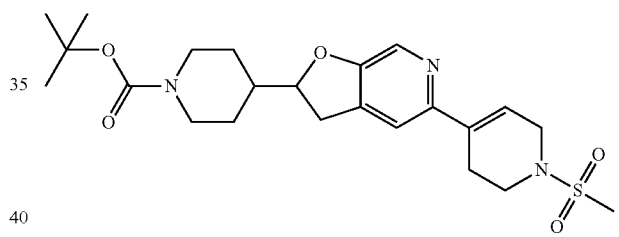

The title compound is prepared from 4-(5-chloro-2,3-dihydro-furo[2,3-c]pyridin-2-yl)-piperidine-1-carboxylic acid tert-butyl ester and 1-methanesulfonyl-4-(4,4,5,5-tetramethyl-[1,3,2]dioxaborolan-2-yl)-1,2,3,6-tetrahydro-pyridine following a procedure analogous to that described for Intermediate 10. LC (method 3): t$_R$=1.12 min; Mass spectrum (ESI$^+$): m/z=464 [M+H]$^+$.

Intermediate 13

5-(1-Methanesulfonyl-1,2,3,6-tetrahydro-pyridin-4-yl)-2-piperidin-4-yl-2,3-dihydro-furo[2,3-c]pyridine

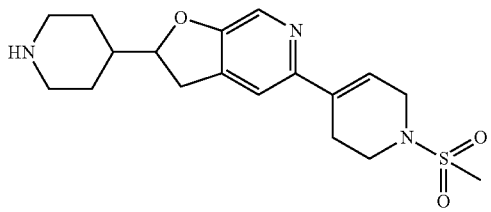 [SMILES: CS(=O)(=O)N1CC=C(c2cc3c(cn2)OC(C2CCNCC2)C3)CC1]

The title compound is prepared from 4-[5-(1-methanesulfonyl-1,2,3,6-tetrahydro-pyridin-4-yl)-2,3-dihydro-furo[2,3-c]pyridin-2-yl]-piperidine-1-carboxylic acid tert-butyl ester following a procedure analogous to that described for Intermediate 11. LC (method 3): $t_R$=0.44 min; Mass spectrum (ESI$^+$): m/z=364 [M+H]$^+$.

Intermediate 14

1-{4-[5-(1-Methanesulfonyl-1,2,3,6-tetrahydro-pyridin-4-yl)-2,3-dihydro-furo[2,3-c]pyridin-2-yl]-piperidin-1-yl}-2-methyl-propan-2-ol

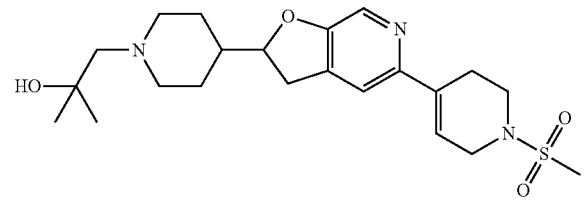 [SMILES: CC(C)(O)CN1CCC(C2Cc3cc(C4=CCN(S(C)(=O)=O)CC4)ncc3O2)CC1]

The title compound is prepared from 5-(1-methanesulfonyl-1,2,3,6-tetrahydro-pyridin-4-yl)-2-piperidin-4-yl-2,3-dihydro-furo[2,3-c]pyridine following a procedure analogous to that described for Intermediate 6. LC (method 3): $t_R$=0.50 min; Mass spectrum (ESI$^+$): m/z=436 [M+H]$^+$.

Intermediate 15

4-[5-(4-Methanesulfonylmethyl-phenyl)-2,3-dihydro-furo[2,3-c]pyridin-2-yl]-piperidine-1-carboxylic acid tert-butyl ester

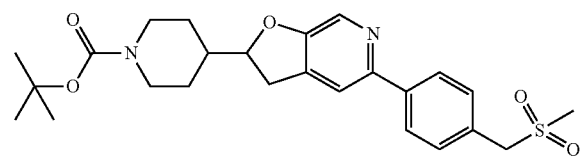 [SMILES: CC(C)(C)OC(=O)N1CCC(C2Cc3cc(-c4ccc(CS(C)(=O)=O)cc4)ncc3O2)CC1]

The title compound is prepared from 4-(5-chloro-2,3-dihydro-furo[2,3-c]pyridin-2-yl)-piperidine-1-carboxylic acid tert-butyl ester and 4-(methanesulfonylmethyl)phenyl boronic acid following a procedure analogous to that described for Intermediate 10. LC (method 1): $t_R$=1.55 min; Mass spectrum (ESI$^+$): m/z=473 [M+H]$^+$.

Intermediate 16

5-(4-Methanesulfonylmethyl-phenyl)-2-piperidin-4-yl-2,3-dihydro-furo[2,3-c]pyridine

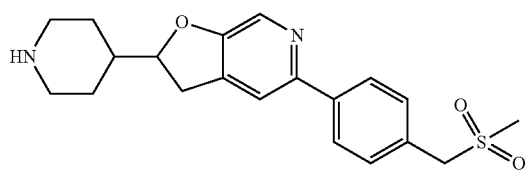 [SMILES: CS(=O)(=O)Cc1ccc(-c2cc3c(cn2)OC(C2CCNCC2)C3)cc1]

The title compound is prepared from 4-[5-(4-methanesulfonylmethyl-phenyl)-2,3-dihydro-furo[2,3-c]pyridin-2-yl]-piperidine-1-carboxylic acid tert-butyl ester following a procedure analogous to that described for Intermediate 11. LC (method 1): $t_R$=0.73 min; Mass spectrum (ESI$^+$): m/z=373 [M+H]$^+$.

Intermediate 17

1-{4-[5-(4-Methanesulfonylmethyl-phenyl)-2,3-dihydro-furo[2,3-c]pyridin-2-yl]-piperidin-1-yl}-2-methyl-propan-2-ol

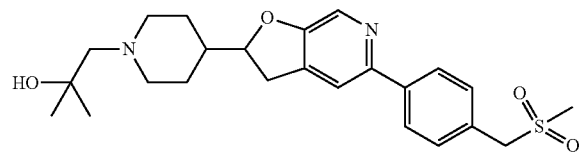 [SMILES: CC(C)(O)CN1CCC(C2Cc3cc(-c4ccc(CS(C)(=O)=O)cc4)ncc3O2)CC1]

The title compound is prepared from 5-(4-methanesulfonylmethyl-phenyl)-2-piperidin-4-yl-2,3-dihydro-furo[2,3-c]pyridine following a procedure analogous to that described for Intermediate 6. LC (method 1): $t_R$=0.79 min; Mass spectrum (ESI$^+$): m/z=445 [M+H]$^+$.

Intermediate 18

4-[5-(2-Fluoro-4-methanesulfonylmethyl-phenyl)-2,3-dihydro-furo[2,3-c]pyridin-2-yl]-piperidine-1-carboxylic acid tert-butyl ester

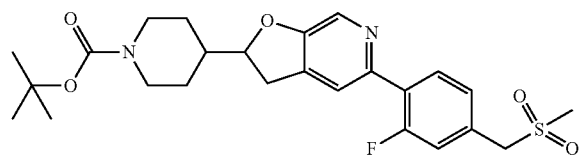 [SMILES: CC(C)(C)OC(=O)N1CCC(C2Cc3cc(-c4ccc(CS(C)(=O)=O)cc4F)ncc3O2)CC1]

The title compound is prepared from 4-(5-chloro-2,3-dihydro-furo[2,3-c]pyridin-2-yl)-piperidine-1-carboxylic acid tert-butyl ester and 2-(2-fluoro-4-methanesulfonylmethyl-phenyl)-4,4,5,5-tetramethyl-[1,3,2]dioxaborolane following a procedure analogous to that described for Intermediate 10. LC (method 1): $t_R$=1.61 min; Mass spectrum (ESI$^+$): m/z=491 [M+H]$^+$.

Intermediate 19

5-(2-Fluoro-4-methanesulfonylmethyl-phenyl)-2-piperidin-4-yl-2,3-dihydro-furo[2,3-c]pyridine

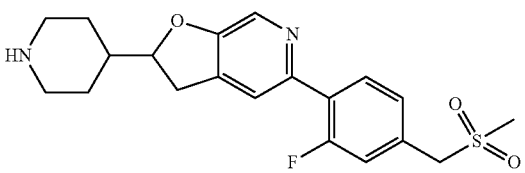 [SMILES: CS(=O)(=O)Cc1ccc(-c2cc3c(cn2)OC(C2CCNCC2)C3)c(F)c1]

The title compound is prepared from 4-[5-(2-fluoro-4-methanesulfonylmethyl-phenyl)-2,3-dihydro-furo[2,3-c]pyridin-2-yl]-piperidine-1-carboxylic acid tert-butyl ester following a procedure analogous to that described for Intermediate 11. LC (method 1): $t_R$=0.78 min; Mass spectrum (ESI$^+$): m/z=391 [M+H]$^+$.

Intermediate 20

1-{4-[5-(2-Fluoro-4-methanesulfonylmethyl-phenyl)-2,3-dihydro-furo[2,3-c]pyridin-2-yl]-piperidin-1-yl}-2-methyl-propan-2-ol

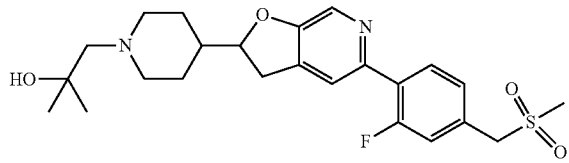 [SMILES: CC(C)(O)CN1CCC(C2Cc3cc(-c4ccc(CS(C)(=O)=O)cc4F)ncc3O2)CC1]

The title compound is prepared from 5-(2-fluoro-4-methanesulfonylmethyl-phenyl)-2-piperidin-4-yl-2,3-dihydro-furo[2,3-c]pyridine following a procedure analogous to that described for Intermediate 6. LC (method 1): $t_R$=0.85 min; Mass spectrum (ESI$^+$): m/z=463 [M+H]$^+$.

Intermediate 21

4-[2-(5-Bromo-2-chloro-pyridin-4-yl)-1-hydroxy-1-methyl-ethyl]-piperidine-1-carboxylic acid tert-butyl ester

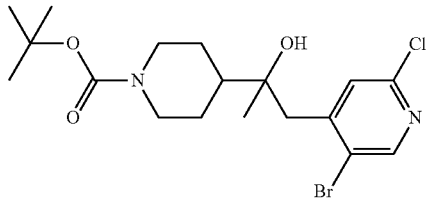 [SMILES: CC(C)(C)OC(=O)N1CCC(C(C)(O)Cc2cc(Cl)ncc2Br)CC1]

A solution of 4-[2-(5-bromo-2-chloro-pyridin-4-yl)-acetyl]-piperidine-1-carboxylic acid tert-butyl ester (9.80 g) in tetrahydrofuran (6 mL) is added dropwise to an ice cooled solution of methyl magnesium bromide (1.4 M in toluene/tetrahydrofuran 75:25, 74 mL). The reaction mixture is stirred for 30 min in the cooling bath and then at room temperature for 1 h. The mixture is poured into aqueous NH$_4$Cl solution and extracted with ethyl acetate. The combined extracts are dried over MgSO$_4$ and concentrated in vacuo. Since the residue still contains a considerable amount of starting material, it is azeotropically dried using toluene and resubmitted to the procedure described above. The crude product is purified by preparative HPLC (column: Waters X-Bridge C18; mobile phase: water+0.125% NH$_4$OH/methanol 90:10→100:0) to give the title compound. LC (method 4): $t_R$=1.33 min; Mass spectrum (ESI$^+$): m/z=433, 435 [M+H]$^+$.

Intermediate 22

4-(5-Chloro-2-methyl-2,3-dihydro-furo[2,3-c]pyridin-2-yl)-piperidine-1-carboxylic acid tert-butyl ester

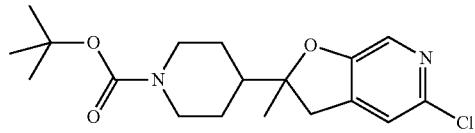 [SMILES: CC(C)(C)OC(=O)N1CCC(C2(C)Cc3cc(Cl)ncc3O2)CC1]

The title compound is prepared from 4-[2-(5-bromo-2-chloro-pyridin-4-yl)-1-hydroxy-1-methyl-ethyl]-piperidine-1-carboxylic acid tert-butyl ester following a procedure analogous to that described for Intermediate 9. LC (method 4): $t_R$=1.29 min; Mass spectrum (ESI$^+$): m/z=353 [M+H]$^+$.

Intermediate 23 and 24

(S)-4-(5-Chloro-2-methyl-2,3-dihydro-furo[2,3-c]pyridin-2-yl)-piperidine-1-carboxylic acid tert-butyl ester and (R)-4-(5-Chloro-2-methyl-2,3-dihydro-furo[2,3-c]pyridin-2-yl)-piperidine-1-carboxylic acid tert-butyl ester

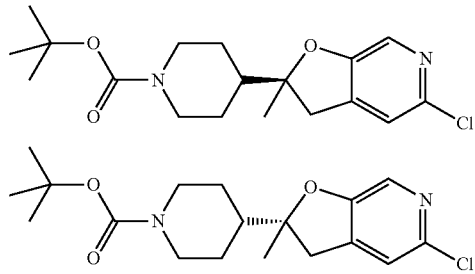

The title compounds are obtained in separate fractions upon SFC on chiral phase of racemic Intermediate 22 (column: Daicel IC, 250×20 mm; mobile phase: methanol containing 0.2% diethylamine/sc carbon dioxide 25:75; flow rate 60 ml/min). The configurations of the stereocenters of Intermediates 23 and 24 were unambiguously determined by X-ray analysis of the crystal structure of a derivative of Intermediate 23, (S)-2-[1-(5-bromo-pyrimidin-2-yl)-piperidin-4-yl]-5-chloro-2,3-dihydro-furo[2,3-c]pyridine (obtained upon acid induced liberation of the piperidine N of Intermediate 23 and its subsequent derivatization with 5-bromo-2-chloro-pyrimidine); retention times on the SFC on chiral phase (Daicel IC, 250×4.6 mm; mobile phase: methanol containing 0.2% diethylamine/sc carbon dioxide 25:75; flow rate 4 ml/min): Intermediate 23: $t_R$=3.77 min; Intermediate 24: $t_R$=4.42 min.

Intermediate 25

(R)-4-[5-(4-Methanesulfonyl-phenyl)-2-methyl-2,3-dihydro-furor[2,3-c]pyridin-2-yl]-piperidine-1-carboxylic acid tert-butyl ester

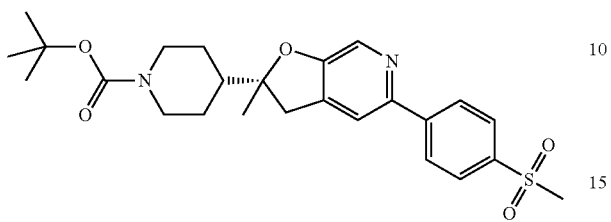

The title compound is prepared from (S)-4-(5-chloro-2-methyl-2,3-dihydro-furo[2,3-c]pyridin-2-yl)-piperidine-1-carboxylic acid tert-butyl ester and 4-(methanesulfonyl)phenylboronic acid following a procedure analogous to that described for Intermediate 10. LC (method 4): $t_R$=1.19 min; Mass spectrum (ESI$^+$): m/z=473 [M+H]$^+$.

Intermediate 26

(R)-5-(4-Methanesulfonyl-phenyl)-2-methyl-2-piperidin-4-yl-2,3-dihydro-furo[2,3-c]pyridine

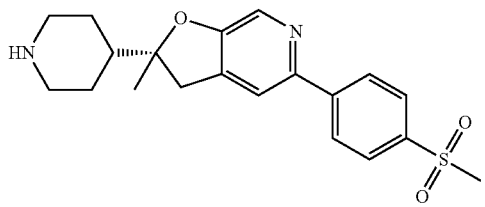 [SMILES: C[C@]1(C2CCNCC2)Cc2cc(-c3ccc(S(C)(=O)=O)cc3)ncc2O1]

The title compound is prepared from (S)-4-[5-(4-methanesulfonyl-phenyl)-2-methyl-2,3-dihydro-furo[2,3-c]pyridin-2-yl]-piperidine-1-carboxylic acid tert-butyl ester following a procedure analogous to that described for Intermediate 11. LC (method 4): $t_R$=0.63 min; Mass spectrum (ESI$^+$): m/z=373 [M+H]$^+$.

Intermediate 27

(R)-1-{4-[5-(4-Methanesulfonyl-phenyl)-2-methyl-2,3-dihydro-furo[2,3-c]pyridin-2-yl]-piperidin-1-yl}-2-methyl-propan-2-ol

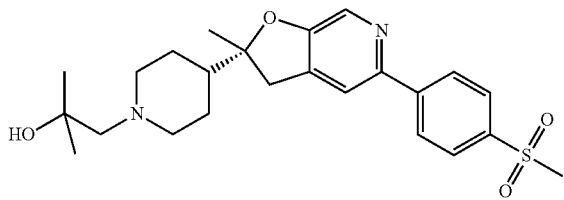 [SMILES: CC(C)(O)CN1CCC([C@@]2(C)Cc3cc(-c4ccc(S(C)(=O)=O)cc4)ncc3O2)CC1]

The title compound is prepared from (S)-5-(4-methanesulfonyl-phenyl)-2-methyl-2-piperidin-4-yl-2,3-dihydro-furo[2,3-c]pyridine following a procedure analogous to that described for Intermediate 6. LC (method 4): $t_R$=0.67 min; Mass spectrum (ESI$^+$): m/z=445 [M+H]$^+$.

Intermediate 28 and 29

(R)-4-(5-Chloro-2,3-dihydro-furo[2,3-c]pyridin-2-yl)-piperidine-1-carboxylic acid tert-butyl ester and (S)-4-(5-Chloro-2,3-dihydro-furo[2,3-c]pyridin-2-yl)-piperidine-1-carboxylic acid tert-butyl ester

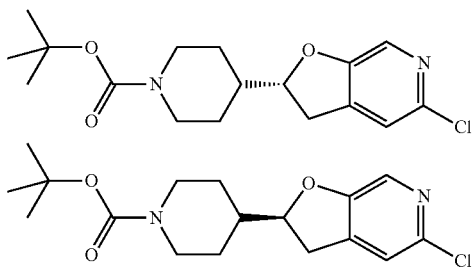

The title compounds are obtained in separate fractions upon SFC on chiral phase of racemic Intermediate 9 (column: Daicel IC, 250×20 mm; mobile phase: ethanol containing 0.2% diethylamine/sc carbon dioxide 25:75; flow rate 50 ml/min). The configurations of the stereocenters of Intermediates 28 and 29 were unambiguously determined by X-ray analysis of a crystal structure of Intermediate 29; retention times on the SFC on chiral phase (Daicel IC, 250×4.6 mm; mobile phase: ethanol containing 0.2% diethylamine/sc carbon dioxide 25:75; flow rate 4 ml/min): Intermediate 28: $t_R$=1.64 min; Intermediate 29: $t_R$=1.91 min.

Intermediate 30

(S)-4-[5-(1-Methanesulfonyl-1,2,3,6-tetrahydro-pyridin-4-yl)-2,3-dihydro-furo[2,3-c]pyridin-2-yl]-piperidine-1-carboxylic acid tert-butyl ester

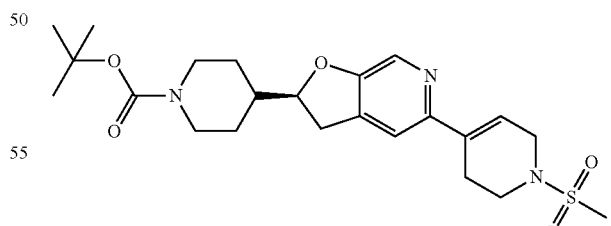

The title compound is prepared from (S)-4-(5-chloro-2,3-dihydro-furo[2,3-c]pyridin-2-yl)-piperidine-1-carboxylic acid tert-butyl ester and 1-methanesulfonyl-4-(4,4,5,5-tetramethyl-[1,3,2]dioxaborolan-2-yl)-1,2,3,6-tetrahydro-pyridine following a procedure analogous to that described for Intermediate 10. LC (method 3): $t_R$=1.10 min; Mass spectrum (ESI$^+$): m/z=464 [M+H]$^+$.

Intermediate 31

(S)-5-(1-Methanesulfonyl-1,2,3,6-tetrahydro-pyridin-4-yl)-2-piperidin-4-yl-2,3-dihydro-furo[2,3-c]pyridine

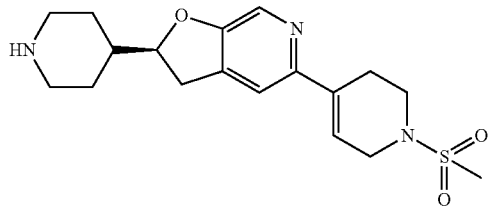 [SMILES: CS(=O)(=O)N1CC=C(c2cc3c(cn2)O[C@H](C2CCNCC2)C3)CC1]

The title compound is prepared from (S)-4-[5-(1-methanesulfonyl-1,2,3,6-tetrahydro-pyridin-4-yl)-2,3-dihydro-furo[2,3-c]pyridin-2-yl]-piperidine-1-carboxylic acid tert-butyl ester following a procedure analogous to that described for Intermediate 11. LC (method 3): $t_R$=0.44 min; Mass spectrum (ESI$^+$): m/z=364 [M+H]$^+$.

Intermediate 32

(S)-1-{4-[5-(1-Methanesulfonyl-1,2,3,6-tetrahydro-pyridin-4-yl)-2,3-dihydro-furo[2,3-c]pyridin-2-yl]-piperidin-1-yl}-2-methyl-propan-2-ol

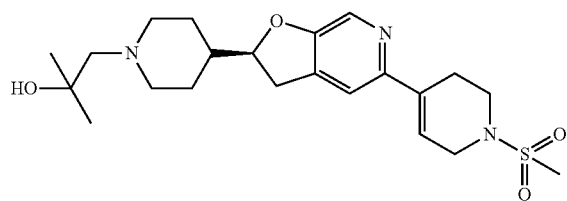 [SMILES: CC(C)(O)CN1CCC([C@@H]2Cc3cc(C4=CCN(S(C)(=O)=O)CC4)ncc3O2)CC1]

The title compound is prepared from (S)-5-(1-methanesulfonyl-1,2,3,6-tetrahydro-pyridin-4-yl)-2-piperidin-4-yl-2,3-dihydro-furo[2,3-c]pyridine following a procedure analogous to that described for Intermediate 6. LC (method 3): $t_R$=0.50 min; Mass spectrum (ESI$^+$): m/z=436 [M+H]$^+$.

Intermediate 33

(R)-4-[5-(1-Methanesulfonyl-1,2,3,6-tetrahydro-pyridin-4-yl)-2,3-dihydro-furo[2,3-c]pyridin-2-yl]-piperidine-1-carboxylic acid tert-butyl ester

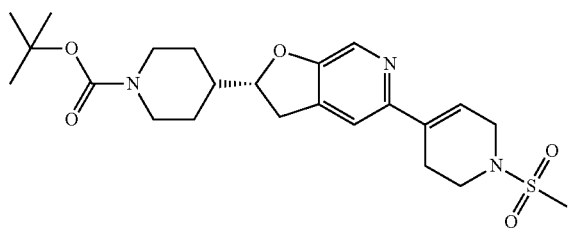

The title compound is prepared from (R)-4-(5-chloro-2,3-dihydro-furo[2,3-c]pyridin-2-yl)-piperidine-1-carboxylic acid tert-butyl ester and 1-methanesulfonyl-4-(4,4,5,5-tetramethyl-[1,3,2]dioxaborolan-2-yl)-1,2,3,6-tetrahydro-pyridine following a procedure analogous to that described for Intermediate 10. LC (method 3): $t_R$=1.10 min; Mass spectrum (ESI$^+$): m/z=464 [M+H]$^+$.

Intermediate 34

(R)-5-(1-Methanesulfonyl-1,2,3,6-tetrahydro-pyridin-4-yl)-2-piperidin-4-yl-2,3-dihydro-furo[2,3-c]pyridine

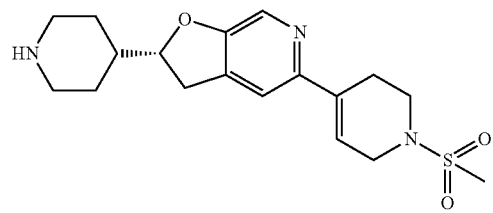 [SMILES: CS(=O)(=O)N1CC=C(c2cc3c(cn2)O[C@@H](C2CCNCC2)C3)CC1]

The title compound is prepared from (R)-4-[5-(1-methanesulfonyl-1,2,3,6-tetrahydro-pyridin-4-yl)-2,3-dihydro-furo[2,3-c]pyridin-2-yl]-piperidine-1-carboxylic acid tert-butyl ester following a procedure analogous to that described for Intermediate 11. LC (method 3): $t_R$=0.44 min; Mass spectrum (ESI$^+$): m/z=364 [M+H]$^+$.

Intermediate 35

(R)-1-{4-[5-(1-Methanesulfonyl-1,2,3,6-tetrahydro-pyridin-4-yl)-2,3-dihydro-furo[2,3-c]pyridin-2-yl]-piperidin-1-yl}-2-methyl-propan-2-ol

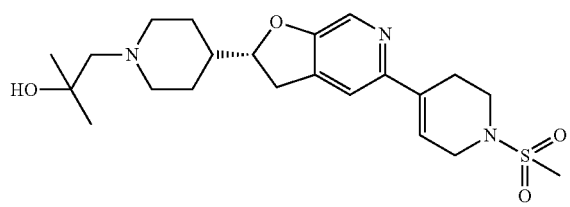 [SMILES: CC(C)(O)CN1CCC([C@H]2Cc3cc(C4=CCN(S(C)(=O)=O)CC4)ncc3O2)CC1]

The title compound is prepared from (R)-5-(1-methanesulfonyl-1,2,3,6-tetrahydro-pyridin-4-yl)-2-piperidin-4-yl-2,3-dihydro-furo[2,3-c]pyridine following a procedure analogous to that described for Intermediate 6. LC (method 3): $t_R$=0.50 min; Mass spectrum (ESI$^+$): m/z=436 [M+H]$^+$.

Intermediate 36

(R)-4-[5-(1-Methanesulfonyl-1,2,3,6-tetrahydro-pyridin-4-yl)-2-methyl-2,3-dihydro-furo[2,3-c]pyridin-2-yl]-piperidine-1-carboxylic acid tert-butyl ester

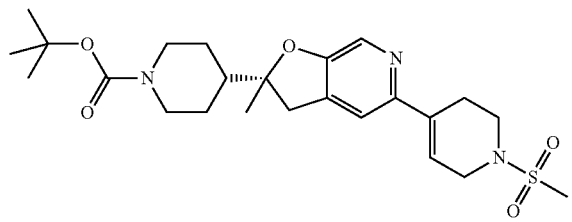 [SMILES: CC(C)(C)OC(=O)N1CCC([C@@]2(C)Cc3cc(C4=CCN(S(C)(=O)=O)CC4)ncc3O2)CC1]

The title compound is prepared from (S)-4-(5-chloro-2-methyl-2,3-dihydro-furo[2,3-c]pyridin-2-yl)-piperidine-1-carboxylic acid tert-butyl ester and 1-methanesulfonyl-4-(4,4,5,5-tetramethyl-[1,3,2]dioxaborolan-2-yl)-1,2,3,6-tetrahydro-pyridine following a procedure analogous to that described for Intermediate 10. LC (method 4): $t_R$=1.02 min; Mass spectrum (ESI$^+$): m/z=478 [M+H]$^+$.

Intermediate 37

(R)-5-(1-Methanesulfonyl-1,2,3,6-tetrahydro-pyridin-4-yl)-2-methyl-2-piperidin-4-yl-2,3-dihydro-furo[2,3-c]pyridine

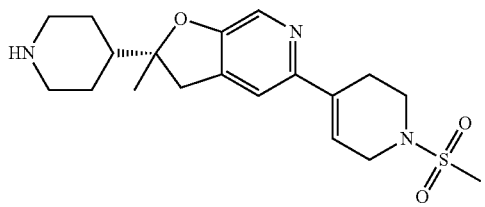 [SMILES: C[C@]1(C2CCNCC2)Cc2cc(C3=CCN(S(C)(=O)=O)CC3)ncc2O1]

The title compound is prepared from (S)-4-[5-(1-methanesulfonyl-1,2,3,6-tetrahydro-pyridin-4-yl)-2-methyl-2,3-dihydro-furo[2,3-c]pyridin-2-yl]-piperidine-1-carboxylic acid tert-butyl ester following a procedure analogous to that described for Intermediate 11. LC (method 4): $t_R$=0.48 min; Mass spectrum (ESI$^+$): m/z=378 [M+H]$^+$.

Intermediate 38

(R)-1-{4-[5-(1-Methanesulfonyl-1,2,3,6-tetrahydro-pyridin-4-yl)-2-methyl-2,3-dihydro-furo[2,3-c]pyridin-2-yl]-piperidin-1-yl}-2-methyl-propan-2-ol

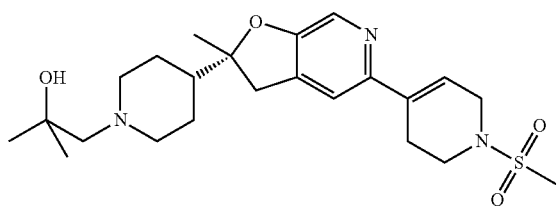 [SMILES: CC(C)(O)CN1CCC([C@@]2(C)Cc3cc(C4=CCN(S(C)(=O)=O)CC4)ncc3O2)CC1]

The title compound is prepared from (S)-5-(1-methanesulfonyl-1,2,3,6-tetrahydro-pyridin-4-yl)-2-methyl-2-piperidin-4-yl-2,3-dihydro-furo[2,3-c]pyridine following a procedure analogous to that described for Intermediate 6. LC (method 4): $t_R$=0.55 min; Mass spectrum (ESI$^+$): m/z=450 [M+H]$^+$.

Intermediate 39

(R)-4-[5-(4-Methanesulfonyl-phenyl)-2,3-dihydro-furo[2,3-c]pyridin-2-yl]-piperidine-1-carboxylic acid tert-butyl ester

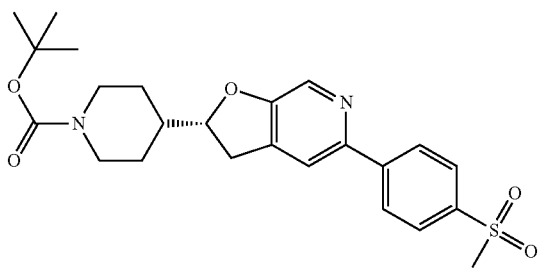 [SMILES: CC(C)(C)OC(=O)N1CCC([C@H]2Cc3cc(-c4ccc(S(C)(=O)=O)cc4)ncc3O2)CC1]

The title compound is prepared from (R)-4-(5-chloro-2,3-dihydro-furo[2,3-c]pyridin-2-yl)-piperidine-1-carboxylic acid tert-butyl ester and 4-(methanesulfonyl)phenylboronic acid following a procedure analogous to that described for Intermediate 10. LC (method 1): $t_R$=1.68 min; Mass spectrum (ESI$^+$): m/z=459 [M+H]$^+$.

Intermediate 40

(R)-5-(4-Methanesulfonyl-phenyl)-2-piperidin-4-yl-2,3-dihydro-furo[2,3-c]pyridine

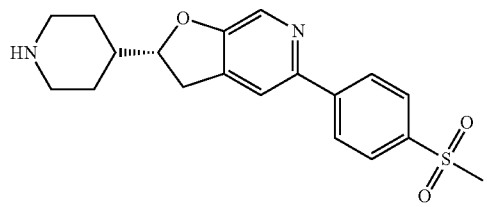 [SMILES: CS(=O)(=O)c1ccc(-c2cc3c(cn2)O[C@@H](C2CCNCC2)C3)cc1]

The title compound is prepared from (R)-4-[5-(4-methanesulfonyl-phenyl)-2,3-dihydro-furo[2,3-c]pyridin-2-yl]-piperidine-1-carboxylic acid tert-butyl ester following a procedure analogous to that described for Intermediate 11. LC (method 1): $t_R$=0.90 min; Mass spectrum (ESI$^+$): m/z=359 [M+H]$^+$.

Intermediate 41

(R)-1-{4-[5-(4-Methanesulfonyl-phenyl)-2,3-dihydro-furo[2,3-c]pyridin-2-yl]-piperidin-1-yl}-2-methyl-propan-2-ol

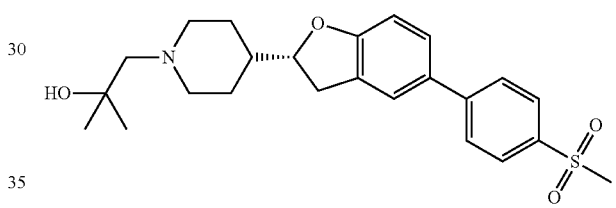

The title compound is prepared from (R)-5-(1-methanesulfonyl-1,2,3,6-tetrahydro-pyridin-4-yl)-2-methyl-2-piperidin-4-yl-2,3-dihydro-furo[2,3-c]pyridine following a procedure analogous to that described for Intermediate 6. LC (method 1): $t_R$=0.91 min; Mass spectrum (ESI$^+$): m/z=431 [M+H]$^+$.

Example 1

1-(2-Fluoro-2-methyl-propyl)-4-[5-(4-methanesulfonyl-phenyl)-2,3-dihydro-benzofuran-2-yl]-piperidine

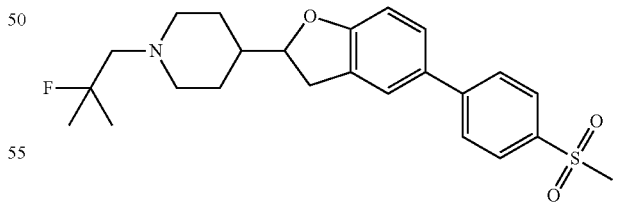

A solution of [bis(2-methoxyethyl)amino]sulfur trifluoride in toluene (50%; 162 μL) is added to an ice-cooled solution of 1-{4-[5-(4-methanesulfonyl-phenyl)-2,3-dihydro-benzofuran-2-yl]-piperidin-1-yl}-2-methyl-propan-2-ol (100 mg) in dichloromethane (2 mL) and the resulting mixture is stirred for 16 h. The reaction mixture is diluted with methanol and concentrated in vacuo. The residue is purified by HPLC to give the title compound. LC (method 1): $t_R$=1.17 min; Mass spectrum (ESI$^+$): m/z=432 [M+H]$^+$.

Example 2

5-(4-Methanesulfonyl-phenyl)-2-{1-[(1-trifluoromethyl-cyclopropyl)methyl]-piperidin-4-yl}-2,3-dihydro-furo[2,3-c]pyridine

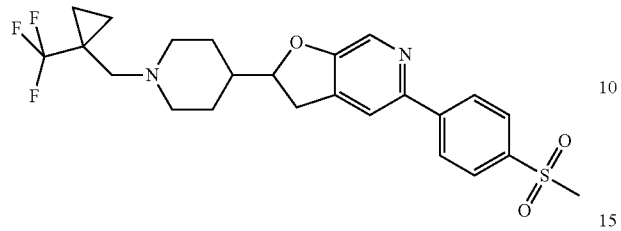

A mixture of 5-(4-methanesulfonyl-phenyl)-2-piperidin-4-yl-2,3-dihydro-furo[2,3-c]pyridine (435 mg), methanesulfonic acid (1-trifluoromethyl-cyclopropyl)methyl ester (700 mg), potassium carbonate (850 mg), and potassium iodide (100 mg) in N-methyl-2-pyrrolidone (8 mL) is stirred at 100° C. for 4 h and then at room temperature overnight. The solvent is evaporated and the residue is triturated with methanol and filtered. The filtrate is concentrated in vacuo and the residue is purified by HPLC to give the title compound. LC (method 1): $t_R$=1.09 min; Mass spectrum (ESI$^+$): m/z=481 [M+H]$^+$.

Example 3

2-[1-(2-Fluoro-2-methyl-propyl)-piperidin-4-yl]-5-(1-methanesulfonyl-1,2,3,6-tetrahydro-pyridin-4-yl)-2,3-dihydro-furo[2,3-c]pyridine

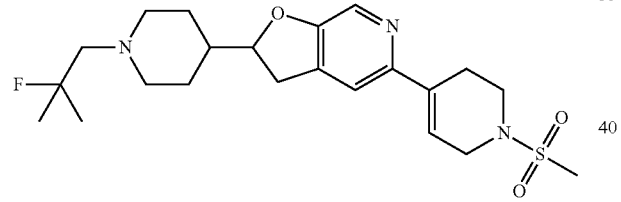

The title compound is prepared from 1-{4-[5-(1-methanesulfonyl-1,2,3,6-tetrahydro-pyridin-4-yl)-2,3-dihydro-furo[2,3-c]pyridin-2-yl]-piperidin-1-yl}-2-methyl-propan-2-ol following a procedure analogous to that described in Example 1. LC (method 3): $t_R$=0.62 min; Mass spectrum (ESI$^+$): m/z=438 [M+H]$^+$.

Example 4

2-[1-(2-Fluoro-2-methyl-propyl)-piperidin-4-yl]-5-(4-methanesulfonylmethyl-phenyl)-2,3-dihydro-furo[2,3-c]pyridine

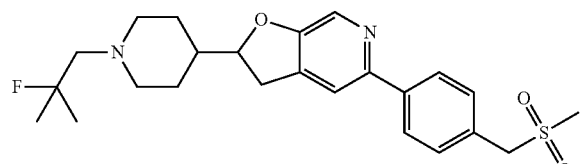

The title compound is prepared from 1-{4-[5-(4-methanesulfonylmethyl-phenyl)-2,3-dihydro-furo[2,3-c]pyridin-2-yl]-piperidin-1-yl}-2-methyl-propan-2-ol following a procedure analogous to that described in Example 1. LC (method 1): $t_R$=0.86 min; Mass spectrum (ESI$^+$): m/z=447 [M+H]$^+$.

Example 5

2-[1-(2-Fluoro-2-methyl-propyl)-piperidin-4-yl]-5-(1-methanesulfonyl-piperidin-4-yl)-2,3-dihydro-furo[2,3-c]pyridine

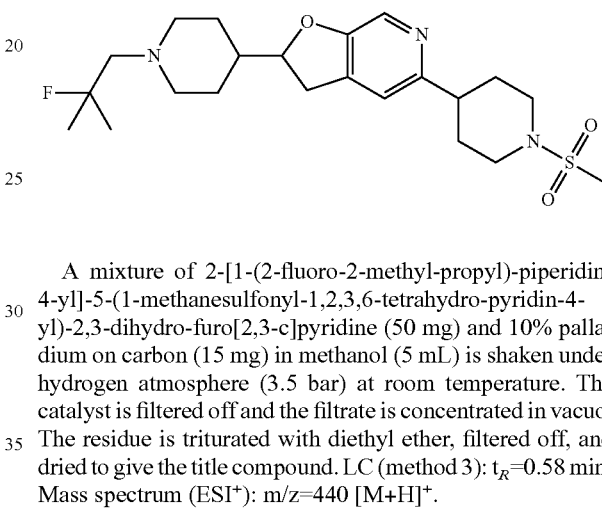

A mixture of 2-[1-(2-fluoro-2-methyl-propyl)-piperidin-4-yl]-5-(1-methanesulfonyl-1,2,3,6-tetrahydro-pyridin-4-yl)-2,3-dihydro-furo[2,3-c]pyridine (50 mg) and 10% palladium on carbon (15 mg) in methanol (5 mL) is shaken under hydrogen atmosphere (3.5 bar) at room temperature. The catalyst is filtered off and the filtrate is concentrated in vacuo. The residue is triturated with diethyl ether, filtered off, and dried to give the title compound. LC (method 3): $t_R$=0.58 min; Mass spectrum (ESI$^+$): m/z=440 [M+H]$^+$.

Example 6

5-(1-Methanesulfonyl-1,2,3,6-tetrahydro-pyridin-4-yl)-2-{1-[(1-trifluoromethyl-cyclopropyl)methyl]-piperidin-4-yl}-2,3-dihydro-furo[2,3-c]pyridine

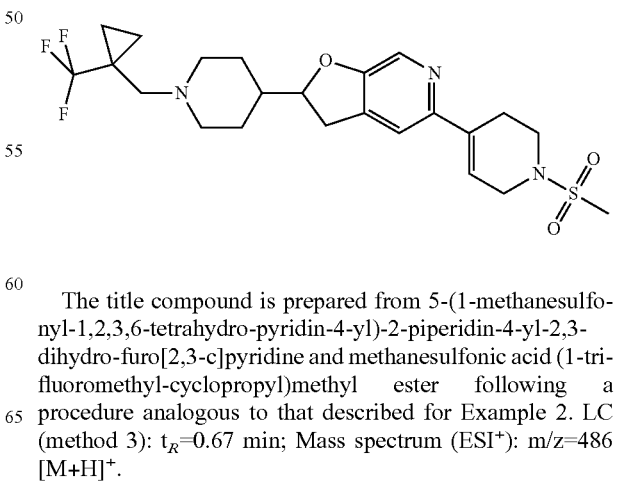

The title compound is prepared from 5-(1-methanesulfonyl-1,2,3,6-tetrahydro-pyridin-4-yl)-2-piperidin-4-yl-2,3-dihydro-furo[2,3-c]pyridine and methanesulfonic acid (1-trifluoromethyl-cyclopropyl)methyl ester following a procedure analogous to that described for Example 2. LC (method 3): $t_R$=0.67 min; Mass spectrum (ESI$^+$): m/z=486 [M+H]$^+$.

Example 7

5-(2-Fluoro-4-methanesulfonylmethyl-phenyl)-2-{1-[(1-trifluoromethyl-cyclopropyl)methyl]-piperidin-4-yl}-2,3-dihydrofuro[2,3-c]pyridine

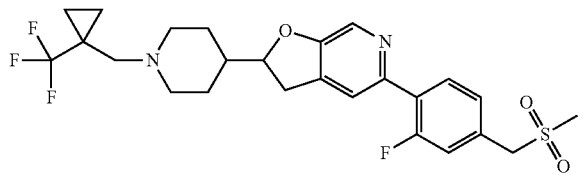 [SMILES: CS(=O)(=O)Cc1ccc(-c2cc3c(cn2)OC(C2CCN(CC4(C(F)(F)F)CC4)CC2)C3)c(F)c1]

The title compound is prepared from 5-(2-fluoro-4-methanesulfonylmethyl-phenyl)-2-piperidin-4-yl-2,3-dihydrofuro[2,3-c]pyridine and methanesulfonic acid (1-trifluoromethyl-cyclopropyl)methyl ester following a procedure analogous to that described for Example 2. LC (method 1): $t_R$=1.01 min; Mass spectrum (ESI$^+$): m/z=513 [M+H]$^+$.

Example 8

5-(4-Methanesulfonylmethyl-phenyl)-2-{1-[(1-trifluoromethyl-cyclopropyl)methyl]-piperidin-4-yl}-2,3-dihydrofuro[2,3-c]pyridine

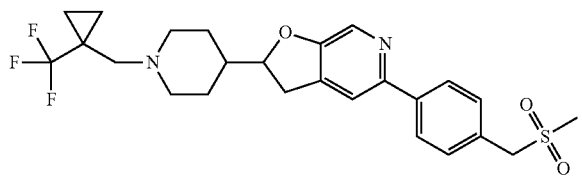 [SMILES: CS(=O)(=O)Cc1ccc(-c2cc3c(cn2)OC(C2CCN(CC4(C(F)(F)F)CC4)CC2)C3)cc1]

The title compound is prepared from 5-(4-methanesulfonylmethyl-phenyl)-2-piperidin-4-yl-2,3-dihydro-furo[2,3-c]pyridine and methanesulfonic acid (1-trifluoromethyl-cyclopropyl)methyl ester following a procedure analogous to that described for Example 2. LC (method 1): $t_R$=0.95 min; Mass spectrum (ESI$^+$): m/z=495 [M+H]$^+$.

Example 9

5-(2-Fluoro-4-methanesulfonylmethyl-phenyl)-2-[1-(2-fluoro-2-methyl-propyl)-piperidin-4-yl]-2,3-dihydro-furo[2,3-c]pyridine

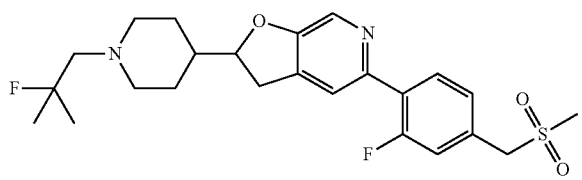 [SMILES: CC(C)(F)CN1CCC(C2Cc3cc(-c4ccc(CS(C)(=O)=O)cc4F)ncc3O2)CC1]

The title compound is prepared from 1-{4-[5-(2-fluoro-4-methanesulfonylmethyl-phenyl)-2,3-dihydro-furo[2,3-c]pyridin-2-yl]-piperidin-1-yl}-2-methyl-propan-2-ol following a procedure analogous to that described in Example 1. LC (method 1): $t_R$=0.96 min; Mass spectrum (ESI$^+$): m/z=465 [M+H]$^+$.

Example 10

(R)-2-[1-(2-Fluoro-2-methyl-propyl)-piperidin-4-yl]-5-(4-methanesulfonyl-phenyl)-2-methyl-2,3-dihydro-furo[2,3-c]pyridine

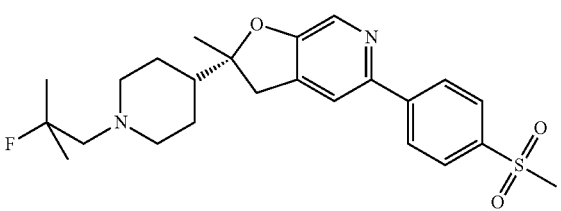 [SMILES: CC(C)(F)CN1CCC([C@@]2(C)Cc3cc(-c4ccc(S(C)(=O)=O)cc4)ncc3O2)CC1]

The title compound is prepared from (S)-1-{4-[5-(4-methanesulfonyl-phenyl)-2-methyl-2,3-dihydro-furo[2,3-c]pyridin-2-yl]-piperidin-1-yl}-2-methyl-propan-2-ol following a procedure analogous to that described in Example 1. LC (method 4): $t_R$=0.73 min; Mass spectrum (ESI$^+$): m/z=447 [M+H]$^+$.

Example 11

(S)-2-[1-(2-Fluoro-2-methyl-propyl)-piperidin-4-yl]-5-(1-methanesulfonyl-1,2,3,6-tetrahydro-pyridin-4-yl)-2,3-dihydro-furo[2,3-c]pyridine

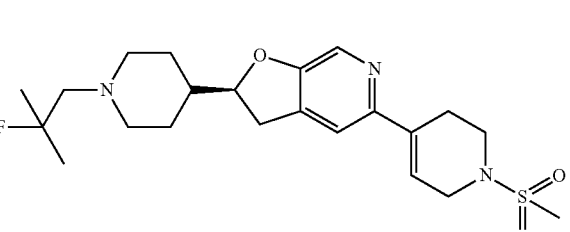

The title compound is prepared from (S)-1-{4-[5-(1-methanesulfonyl-1,2,3,6-tetrahydro-pyridin-4-yl)-2,3-dihydro-furo[2,3-c]pyridin-2-yl]-piperidin-1-yl}-2-methyl-propan-2-ol following a procedure analogous to that described in Example 1. LC (method 3): $t_R$=0.62 min; Mass spectrum (ESI$^+$): m/z=438 [M+H]$^+$.

Example 12

(R)-2-[1-(2-Fluoro-2-methyl-propyl)-piperidin-4-yl]-5-(1-methanesulfonyl-1,2,3,6-tetrahydro-pyridin-4-yl)-2,3-dihydro-furo[2,3-c]pyridine

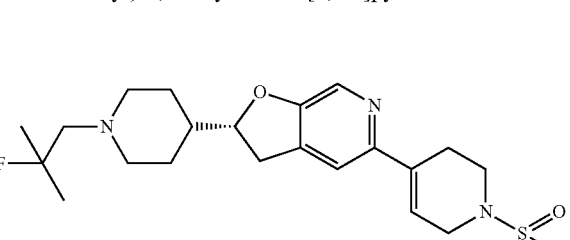

The title compound is prepared from (R)-1-{4-[5-(1-methanesulfonyl-1,2,3,6-tetrahydro-pyridin-4-yl)-2,3-dihydrofuro[2,3-c]pyridin-2-yl]-piperidin-1-yl}-2-methyl-propan-2-ol following a procedure analogous to that described in Example 1. LC (method 3): $t_R$=0.62 min; Mass spectrum (ESI$^+$): m/z=438 [M+H]$^+$.

Example 13

(R)-5-(1-Methanesulfonyl-1,2,3,6-tetrahydro-pyridin-4-yl)-2-methyl-2-{1-[(1-trifluoromethyl-cyclopropyl)methyl]-piperidin-4-yl}-2,3-dihydro-furo[2,3-c]pyridine

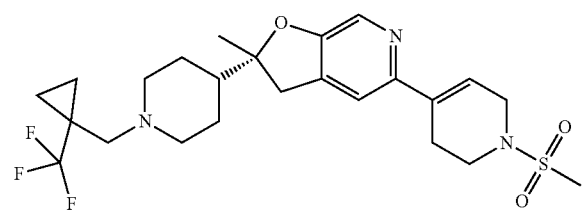 [SMILES: C[C@]1(C2CCN(CC3(C(F)(F)F)CC3)CC2)Cc2cc(C3=CCN(S(C)(=O)=O)CC3)ncc2O1]

The title compound is prepared from (S)-5-(1-methanesulfonyl-1,2,3,6-tetrahydro-pyridin-4-yl)-2-methyl-2-piperidin-4-yl-2,3-dihydro-furo[2,3-c]pyridine and methanesulfonic acid (1-trifluoromethyl-cyclopropyl)methyl ester following a procedure analogous to that described for Example 2. LC (method 4): $t_R$=0.64 min; Mass spectrum (ESI$^+$): m/z=500 [M+H]$^+$.

Example 14 and 15

(R)-5-(1-Methanesulfonyl-1,2,3,6-tetrahydro-pyridin-4-yl)-2-{1-[(1-trifluoromethyl-cyclopropyl)methyl]-piperidin-4-yl}-2,3-dihydro-furo[2,3-c]pyridine and (S)-5-(1-Methanesulfonyl-1,2,3,6-tetrahydro-pyridin-4-yl)-2-{1-[(1-trifluoromethyl-cyclopropyl)methyl]-piperidin-4-yl}-2,3-dihydro-furo[2,3-c]pyridine

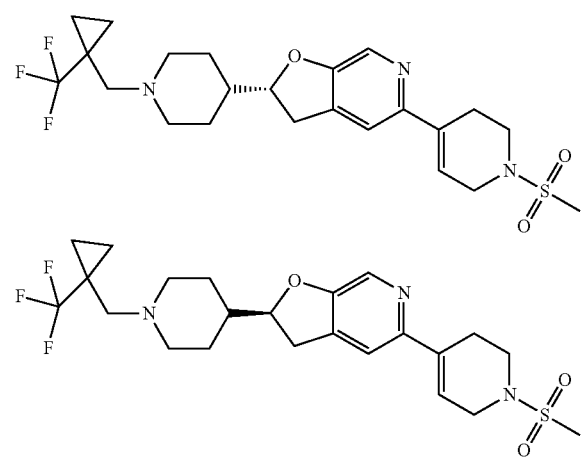

The title compounds are obtained in separate fractions upon SFC on chiral phase of racemic Example 6 (column: Daicel OJH, 250×20 mm; mobile phase: methanol containing 0.2% diethylamine/sc carbon dioxide 20:80; flow rate 10 ml/min). The retention times on the SFC on chiral phase (Daicel OJH, 250×4.6 mm; mobile phase: methanol containing 0.2% diethylamine/sc carbon dioxide 25:75; flow rate 4 ml/min): Example 14: $t_R$=2.70 min; Example 15: $t_R$=3.47 min.

Example 16

(R)-2-[1-(2-Fluoro-2-methyl-propyl)-piperidin-4-yl]-5-(1-methanesulfonyl-1,2,3,6-tetrahydro-pyridin-4-yl)-2-methyl-2,3-dihydro-furo[2,3-c]pyridine

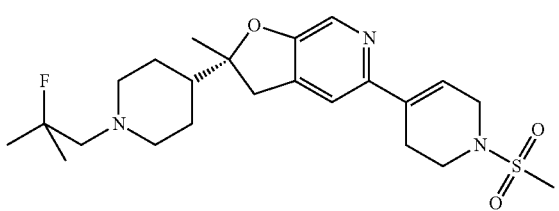 [SMILES: CC(C)(F)CN1CCC([C@@]2(C)Cc3cc(C4=CCN(S(C)(=O)=O)CC4)ncc3O2)CC1]

The title compound is prepared from (S)-1-{4-[5-(1-methanesulfonyl-1,2,3,6-tetrahydro-pyridin-4-yl)-2-methyl-2,3-dihydro-furo[2,3-c]pyridin-2-yl]-piperidin-1-yl}-2-methyl-propan-2-ol following a procedure analogous to that described for Example 1. LC (method 4): $t_R$=0.58 min; Mass spectrum (ESI$^+$): m/z=452 [M+H]$^+$.

Example 17

(R)-5-(4-Methanesulfonyl-phenyl)-2-{1-[(1-trifluoromethyl-cyclopropyl)methyl]-piperidin-4-yl}-2,3-dihydro-furo[2,3-c]pyridine

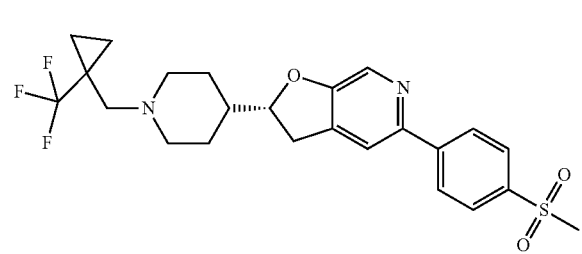 [SMILES: CS(=O)(=O)c1ccc(-c2cc3c(cn2)O[C@@H](C2CCN(CC4(C(F)(F)F)CC4)CC2)C3)cc1]

The title compound is prepared from (R)-5-(4-methanesulfonyl-phenyl)-2-piperidin-4-yl-2,3-dihydro-furo[2,3-c]pyridine and methanesulfonic acid (1-trifluoromethyl-cyclopropyl)methyl ester following a procedure analogous to that described for Example 2. LC (method 1): $t_R$=1.09 min; Mass spectrum (ESI$^+$): m/z=481 [M+H]$^+$.

Example 18

(R)-5-(4-Methanesulfonyl-phenyl)-2-methyl-2-[(1-[(1-trifluoromethyl-cyclopropyl)methyl]-piperidin-4-yl]-2,3-dihydro-furo[2,3-c]pyridine

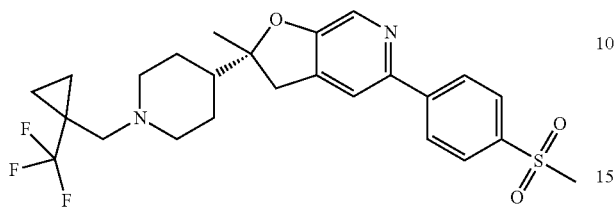

The title compound is prepared from (S)-5-(4-methanesulfonyl-phenyl)-2-methyl-2-piperidin-4-yl-2,3-dihydro-furo[2,3-c]pyridine and methanesulfonic acid (1-trifluoromethyl-cyclopropyl)methyl ester following a procedure analogous to that described for Example 2. LC (method 4): $t_R$=0.79 min; Mass spectrum (ESI$^+$): m/z=495 [M+H]$^+$.

Example 19

(R)-2-[1-(2-Fluoro-2-methyl-propyl)-piperidin-4-yl]-5-(4-methanesulfonyl-phenyl)-2,3-dihydro-furo[2,3-c]pyridine

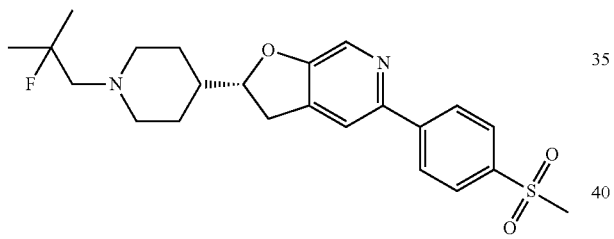

The title compound is prepared from (S)-1-{4-[5-(4-methanesulfonyl-phenyl)-2,3-dihydro-furo[2,3-c]pyridin-2-yl]-piperidin-1-yl}-2-methyl-propan-2-ol following a procedure analogous to that described in Example 1. LC (method 1): $t_R$=1.02 min; Mass spectrum (ESI$^+$): m/z=433 [M+H]$^+$.

The invention claimed is:
1. A compound of formula I

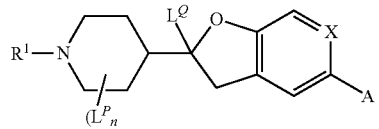

wherein:
$R^1$ is selected from the group $R^1$-G1 consisting of $C_{3-6}$-cycloalkyl-$CH_2$— and linear or branched $C_{1-5}$-alkyl, wherein the $C_{3-6}$-cycloalkyl and the $C_{1-5}$-alkyl groups are optionally substituted with one or more F atoms and/or one $CF_3$ group, and wherein the alkyl group is optionally substituted from position 2 onwards;

A is selected from the group A-G1 consisting of a 1,2,3,6-tetrahydropyridin-4-yl ring substituted at the N with $C_{1-4}$-alkyl-S(=O)$_2$—, a piperidin-4-yl ring substituted at the N with $C_{1-4}$-alkyl-S(=O)$_2$—, and a phenyl ring substituted with a group T and optionally additionally substituted with one or two groups independently selected from F and $CH_3$;

T is selected from the group T-G1 consisting of F, Cl, Br, I, CN, OH, $NO_2$, $C_{1-6}$-alkyl-, $C_{1-6}$-alkenyl-, $C_{1-6}$-alkynyl-, $C_{3-6}$-cycloalkyl, $C_{1-6}$-alkyl-O—, $C_{3-6}$-cycloalkyl-O—, $C_{1-6}$-alkyl-S—, HO—C(=O)—, $C_{1-6}$-alkyl-O—C(=O)—, $C_{1-4}$-alkyl-C(=O)—, $C_{3-6}$-cycloalkyl-C(=O)—, $C_{1-4}$-alkyl-S(=O)—, $C_{1-4}$-alkyl-S(=O)$_2$—, $R^{NT1}R^{NT2}N$—, $R^{NT1}R^{NT2}N$—C(=O)—, $R^{NT1}R^{NT2}N$—S(=O)$_2$—, $R^{NT1}R^{NT2}N$—C(=O)—($R^N$)N—, heterocyclyl, heterocyclyl-O—, aryl, aryl-O—, heteroaryl, and heteroaryl-O—, wherein each alkyl, alkenyl, alkynyl, and cycloalkyl group is optionally substituted with one or more substituents independently selected from F, Cl, CN, OH, $C_{1-3}$-alkyl, $C_{3-6}$-cycloalkyl, $C_{1-3}$-alkyl-O—, $R^{NT1}R^{NT2}N$—, $R^{NT1}R^{NT2}N$—C(=O)—, $C_{1-4}$-alkyl-S(=O)—, $C_{1-4}$-alkyl-S(=O)$_2$—, $R^{NT1}R^{NT2}N$—S(=O)$_2$—, aryl, heteroaryl, and heterocyclyl, wherein aryl is phenyl or naphthyl,
heteroaryl is a 5- or 6-membered aromatic ring which contains 1, 2, 3, or 4 heteroatoms independently selected from N, O, and S, wherein the H-atom in one or more NH groups is optionally replaced by $R^N$,
heterocyclyl is a 4- to 7-membered unsaturated or saturated carbocyclic ring in which 1 or 2 —$CH_2$-groups are independently replaced by $NR^N$, O, —O(=O)—, S, —S(=O)—, or —S(=O)$_2$—, and/or in which a —CH-group is replaced by N, and
each aryl, heteroaryl, or heterocyclyl group is optionally substituted with one or more substituents independently selected from $L^A$;

$R^N$ is independently selected from the group $R^N$-G1 consisting of H, $C_{1-4}$-alkyl, $C_{1-4}$-alkyl-C(=O)—, and $C_{1-4}$-alkyl-S(=O)$_2$—;

$R^{NT1}$ is selected from the group $R^{NT1}$-G1 consisting of H, $C_{1-6}$-alkyl, $C_{3-6}$-cycloalkyl, $C_{1-6}$-alkyl-C(=O)—, $C_{1-6}$-alkyl-S(=O)$_2$, heterocyclyl, aryl, and heteroaryl,
wherein each alkyl and cylcoalkyl group is optionally substituted with one or more substituents independently selected from the group consisting of F, OH, CN, $C_{1-4}$-alkyl, $C_{1-4}$-alkyl-O—, $R^N{}_2N$, $C_{1-4}$-alkyl-S(=O)$_2$—, $C_{3-6}$-cycloalkyl, heterocyclyl, phenyl, and heteroaryl,
heterocyclyl is optionally substituted with one or more substituents independently of each other selected from F, $C_{1-4}$-alkyl, $R^N{}_2N$, OH, and $C_{1-4}$-alkyl-O—,
heterocyclyl is a $C_{4-7}$-cycloalkyl ring in which 1 or 2 —$CH_2$-groups are independently replaced by $NR^N$, O, C(=O), S, S(=O), or S(=O)$_2$,
aryl is phenyl or naphthyl,
heteroaryl is a 5- or 6-membered aromatic ring which contains 1, 2, or 3 heteroatoms independently selected from N, O, and S, wherein the H-atom in one or more NH groups is optionally replaced by $R^N$, and
aryl and heteroaryl are optionally substituted with one or more substituents $L^A$;

$R^{NT2}$ is selected from the group $R^{NT2}$-G1 consisting of H and $C_{1-6}$-alkyl; or $R^{NT1}$ and $R^{NT2}$ are linked to form one group selected from the group $R^{NT1}R^{NT2}$-G1 consisting of a $C_{3-5}$-alkylene group, wherein 1 or 2 —$CH_2$-groups are independently replaced by $NR^N$, O, C(=O), S, S(=O), or $S(=O)_2$, and which are optionally substituted with one or more substituents independently selected from F, $C_{1-4}$-alkyl, $(R^N)_2N$, OH, and $C_{1-4}$-alkyl-O—;

$L^A$ is selected from the group $L^A$-G1 consisting of F, Cl, Br, CN, OH, $NO_2$, $C_{1-4}$-alkyl-, $C_{1-4}$-alkyl-O—, $(R^N)_2N$—C(=O), $(R^N)_2N$—, and $C_{1-4}$-alkyl-$S(=O)_2$—, wherein each alkyl group is optionally substituted with one or more substituents independently selected from F, Cl, CN, OH, and $C_{1-3}$-alkyl-O—;

$L^P$ is selected from the group $L^P$-G1 consisting of F and $C_{1-3}$-alkyl, wherein the alkyl group is optionally substituted with one or more F-atoms;

$L^Q$ is selected from the group $L^Q$-G1 consisting of H and $C_{1-3}$-alkyl;

X is selected from the group X-G1 consisting of CH and N; and n is an integer selected from 0, 1, 2, 3, and 4, or a tautomer, stereoisomer, or salt thereof.

2. The compound according to claim 1, wherein $R^1$ is 2-fluoro-2-methylpropyl or (1-trifluoromethylcyclopropyl)methyl.

3. The compound according to claim 1, wherein:
A is

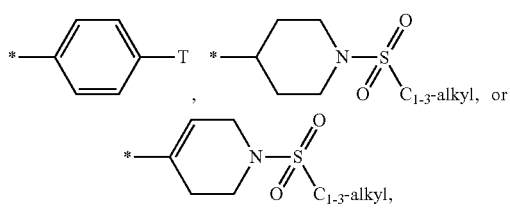

wherein the phenyl group is optionally additionally substituted with one or two groups independently selected from F and $CH_3$.

4. The compound according to claim 1, wherein:
A is

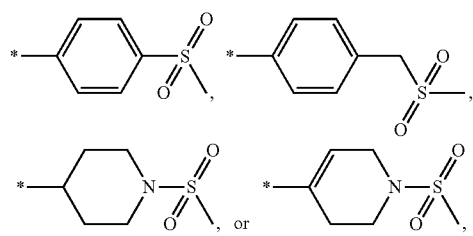

wherein the phenyl groups are optionally substituted with one or two groups independently selected from F and $CH_3$.

5. The compound according to claim 1 wherein:
A is

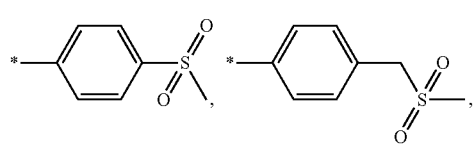

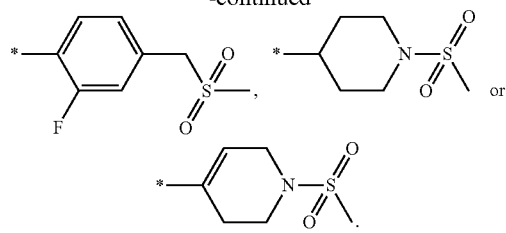

6. The compound according to claim 1, wherein:
X is N;
$R^1$ is

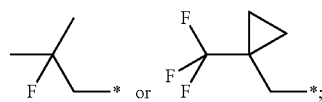

and
A is

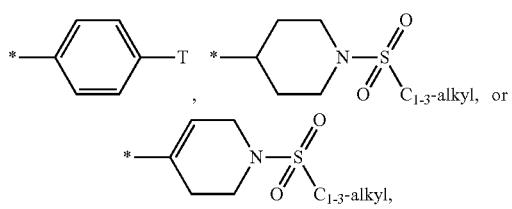

wherein the phenyl group is optionally additionally substituted with one or two groups independently selected from F and $CH_3$;
T is $C_{1-4}$-alkyl-$S(=O)_2$—$CH_2$— or $C_{1-4}$-alkyl-$S(=O)_2$—;
$L^Q$ is H or $CH_3$; and
or a pharmaceutically acceptable salt thereof.

7. The compound according to claim 6, wherein:
A is

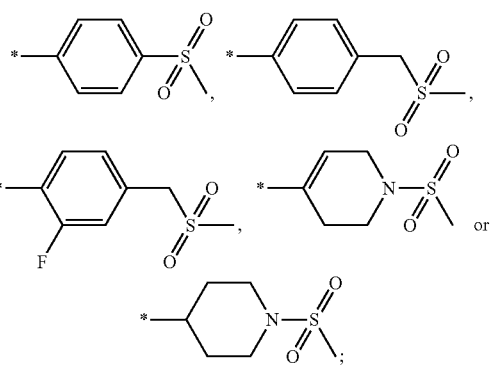

and
$L^Q$ is H or $CH_3$,
or a pharmaceutically acceptable salt thereof.

8. A pharmaceutical composition comprising a compound according to claim 1 and an inert carrier or diluent.

9. A method of treating diabetes, obesity, or dyslipidemia mediated by activating the G-protein-coupled receptor GPR119 in a patient in need thereof, the method comprising administering to the patient a pharmaceutically effective amount of a compound according to claim 1.

\* \* \* \* \*